(12) United States Patent
Parsons et al.

(10) Patent No.: US 11,806,976 B2
(45) Date of Patent: *Nov. 7, 2023

(54) NONWOVEN MATERIAL WITH HIGH CORE BICOMPONENT FIBERS

(71) Applicant: Glatfelter Corporation, Charlotte, NC (US)

(72) Inventors: James B. Parsons, Memphis, TN (US); Alan J. Campbell, Germantown, TN (US); Timothy J. Kistemaker, Mooresville, NC (US); Ronald T. Moose, Lakeland, TN (US); Jacek K. Dutkiewicz, Cordova, TN (US); Brian Fong, Lakeland, TN (US); Thomas J. Cavanaugh, Cordova, TN (US)

(73) Assignee: Glatfelter Corporation, Charlotte, NC (US)

( * ) Notice: Subject to any disclaimer, the term of this patent is extended or adjusted under 35 U.S.C. 154(b) by 374 days.

This patent is subject to a terminal disclaimer.

(21) Appl. No.: 16/651,711

(22) PCT Filed: Sep. 25, 2018

(86) PCT No.: PCT/US2018/052614
§ 371 (c)(1),
(2) Date: Mar. 27, 2020

(87) PCT Pub. No.: WO2019/067432
PCT Pub. Date: Apr. 4, 2019

(65) Prior Publication Data
US 2020/0255992 A1    Aug. 13, 2020

Related U.S. Application Data

(60) Provisional application No. 62/564,108, filed on Sep. 27, 2017.

(51) Int. Cl.
*B32B 5/02* (2006.01)
*D04H 1/541* (2012.01)
(Continued)

(52) U.S. Cl.
CPC .............. *B32B 5/022* (2013.01); *B32B 5/26* (2013.01); *B32B 7/12* (2013.01); *D01F 8/06* (2013.01);
(Continued)

(58) Field of Classification Search
CPC .............. B32B 5/022; B32B 2262/062; B32B 2262/12; B32B 2262/124;
(Continued)

(56) References Cited

U.S. PATENT DOCUMENTS 5,456,982 A * 10/1995 Hansen .................... D04H 1/55
442/364
2006/0154547 A1* 7/2006 Hurley ..................... B08B 1/00
428/296.7
(Continued)

FOREIGN PATENT DOCUMENTS

GB        1406252 A  *  9/1975  ............... D01D 5/30
JP        H1181122 A    3/1999

OTHER PUBLICATIONS

International Search Report and Written Opinion received for PCT patent Application No. PCT/US2018/052614, dated Mar. 12, 2018, 8 pages.

*Primary Examiner* — Jasper Saberi
(74) *Attorney, Agent, or Firm* — Blank Rome LLP

(57) ABSTRACT

Nonwoven materials having at least one layer comprising high core bicomponent fibers are provided. The nonwoven materials can have multiple layers and are suitable for use in a variety of applications, including in absorbent products. The nonwoven materials can have improved resiliency and (Continued)

Figure 1:
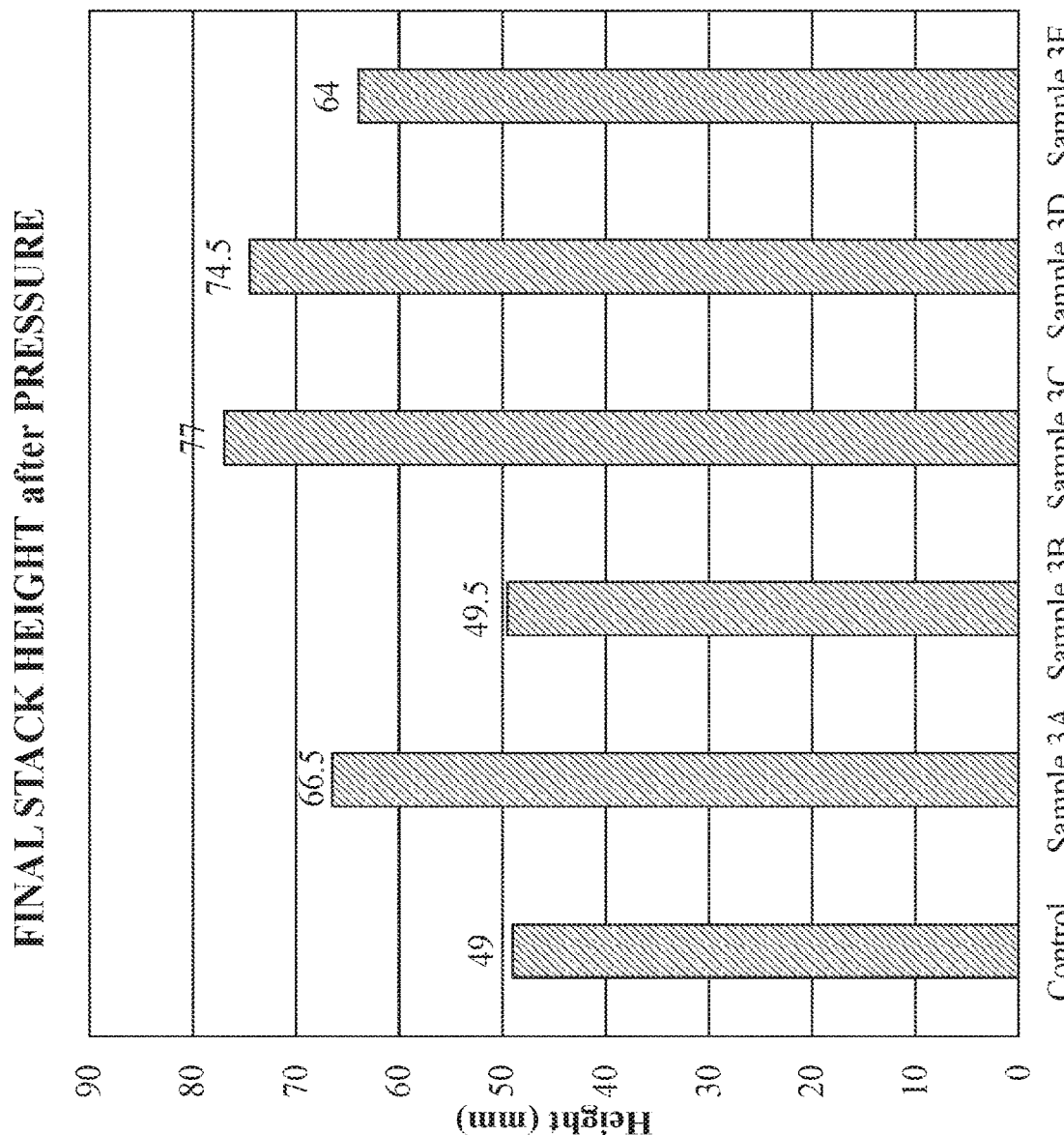

strength and can retain their structure under wetted conditions and after tension and compression.

16 Claims, 18 Drawing Sheets

(51) Int. Cl.
| | |
|---|---|
| *B32B 5/26* | (2006.01) |
| *B32B 7/12* | (2006.01) |
| *D01F 8/06* | (2006.01) |
| *D01F 8/14* | (2006.01) |
| *D04H 1/4291* | (2012.01) |
| *D04H 1/435* | (2012.01) |
| *D04H 1/732* | (2012.01) |
| *D04H 1/4374* | (2012.01) |
| *D04H 1/425* | (2012.01) |
| *A61F 13/53* | (2006.01) |

(52) U.S. Cl.
CPC ............... *D01F 8/14* (2013.01); *D04H 1/425* (2013.01); *D04H 1/4291* (2013.01); *D04H 1/435* (2013.01); *D04H 1/4374* (2013.01); *D04H 1/5412* (2020.05); *D04H 1/5418* (2020.05); *D04H 1/732* (2013.01); *A61F 2013/53024* (2013.01); *A61F 2013/530386* (2013.01); *B32B 2250/02* (2013.01); *B32B 2250/03* (2013.01); *B32B 2255/02* (2013.01); *B32B 2260/021* (2013.01); *B32B 2262/0253* (2013.01); *B32B 2262/0284* (2013.01); *B32B 2262/062* (2013.01); *B32B 2262/12* (2013.01); *B32B 2262/124* (2021.05); *B32B 2262/144* (2021.05); *B32B 2307/726* (2013.01); *B32B 2432/00* (2013.01); *B32B 2555/02* (2013.01)

(58) Field of Classification Search
CPC .......... B32B 2262/144; B32B 2432/00; B32B 2555/02; D04H 1/5412; A61F 2013/53024
See application file for complete search history.

(56) References Cited

U.S. PATENT DOCUMENTS

| | | | |
|---|---|---|---|
| 2008/0085399 | A1 | 4/2008 | Noda et al. |
| 2011/0165470 | A1 | 7/2011 | Dahringer |
| 2012/0144611 | A1* | 6/2012 | Baker ................. D04H 1/44 15/104.93 |
| 2015/0342802 | A1* | 12/2015 | Caputi .............. A61F 13/15658 604/374 |
| 2016/0183758 | A1 | 6/2016 | Baker |
| 2020/0392658 | A1* | 12/2020 | Ren ......................... B32B 5/12 |

* cited by examiner indentations ~1mm into structure
*Drawing not to scale

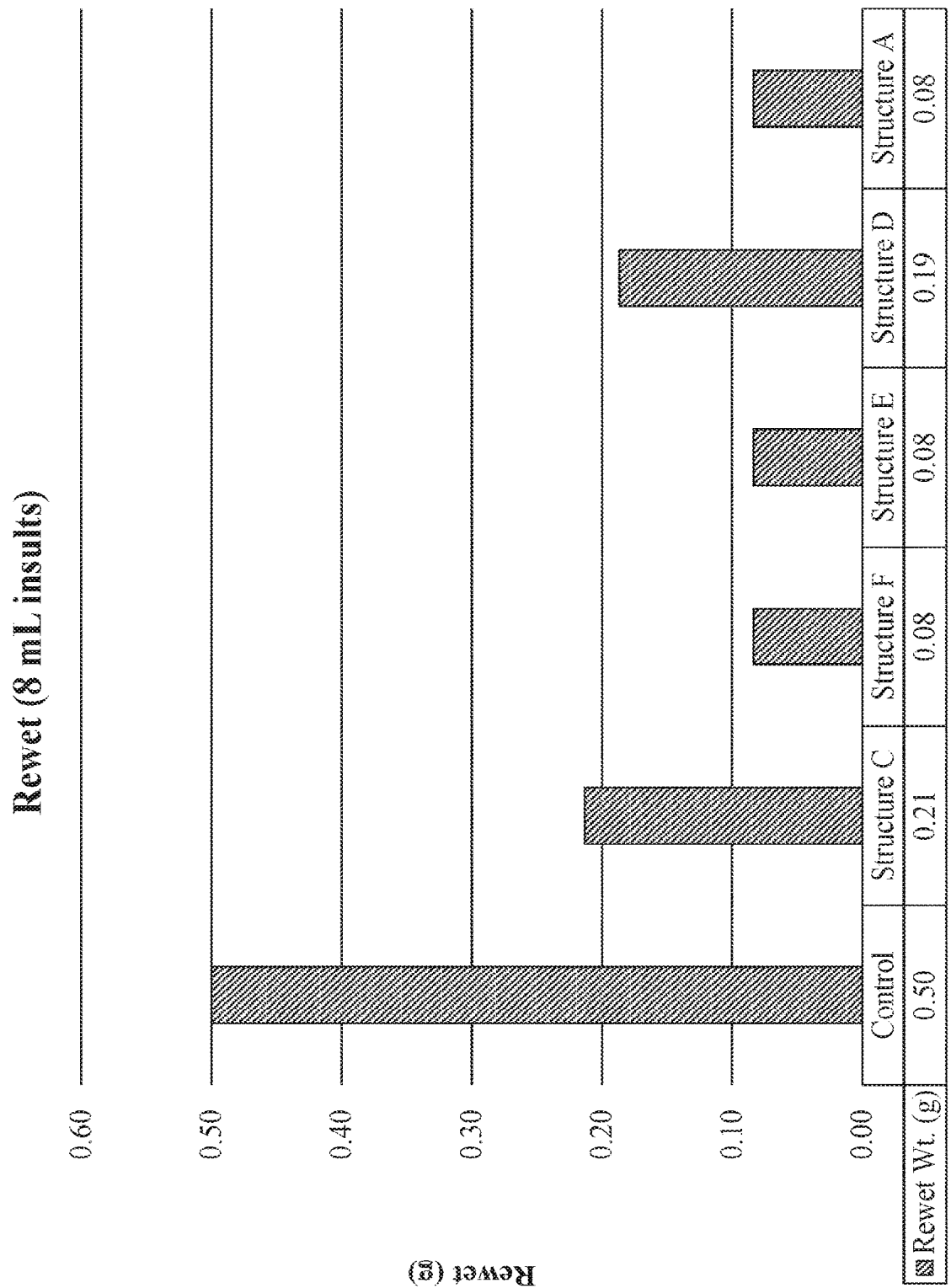

NONWOVEN MATERIAL WITH HIGH CORE BICOMPONENT FIBERS

This application claims the benefit of priority to PCT application serial no. PCT/US2018/052614, filed Sep. 25, 2018 (published as WO/2019/067432, on Apr. 4, 2019), which claims priority to U.S. provisional patent application Ser. No. 62/564,108, filed Sep. 27, 2017, the disclosures of which are hereby incorporated by reference in their entirety.

1. FIELD OF THE INVENTION

Nonwoven materials having at least one layer comprising high core bicomponent fibers are provided. The nonwoven materials can be used for a variety of applications and can have improved resiliency and strength and can retain their structure in wetted conditions and after force is applied.

2. BACKGROUND OF THE INVENTION

Nonwoven structures are important in a, vide range of consumer products, such as absorbent articles including baby diapers, adult incontinence products, sanitary napkins, wipes, and the like. Such nonwoven structures can include various layers and/or components, configured to direct and control the acquisition and retention of fluids. Each of these layers and/or components can include a specific fibrous network that provides the desired functionality. As such, for optimal performance, it can be important to ensure that this fibrous network remains intact during manufacturing and use of the nonwoven material.

For example, nonwoven materials can be used in wipes, e.g., for cleaning various surfaces or applying personal care products. Nonwoven materials made from synthetic and cellulose fibers are particularly suitable for these applications because they can be a disposable and cost-effective single-use alternative to fabric cloths and sponges. However, nonwoven wipes are typically provided to the consumer in a pre-wetted form that is saturated with the desired cleaning or personal care lotion. Fibers, especially natural fibers, can swell and deform upon wetting, which can reduce the integrity and structure of the fibrous network. Moreover, the nonwoven material is subjected to several different compressive and tensile forces during the manufacturing and conversion processes, which can further strain the fibrous network and lead to collapse of the material.

Similarly, in absorbent articles for hygiene applications, various forces are applied during manufacturing and while the material is worn by the user. Moreover, such absorbent articles are typically designed to capture and retain a fluid and therefore may become wet over time. However, if the fibrous network collapses upon use or wetting, the material will be less able to absorb and store additional fluid over time.

Thus, there remains a need in the art for nonwoven materials with improved resilience, in which the fibrous network can maintain its structure upon compressive and tensile forces and while wetted with a liquid. The disclosed subject matter addresses these and other needs.

3. SUMMARY

The presently disclosed subject matter provides for nonwoven materials that include high core bicomponent fibers having a core to sheath ratio of greater than 1:1. Thus, as embodied herein, the present disclosure provides an airlaid nonwoven material comprising high core bicomponent fibers having a polyester core and a polyethylene sheath and a core to sheath ratio of greater than 1:1.

In certain embodiments, the high core bicomponent fibers can have a core to sheath ratio of about 7:3. The airlaid nonwoven material can have a basis weight of from about 30 gsm to about 500 gsm, or from about 50 gsm to about 100 gsm and a caliper of from about 0.1 mm to about 7.5 mm, or from about 0.5 mm to about 1.5 mm. The airlaid nonwoven material can further include low core bicomponent fibers, i.e., bicomponent fibers having a core to sheath ratio of less than 1:1.

In particular embodiments, an airlaid nonwoven material can have at least two layers, including a first layer comprising high core bicomponent fibers and a second layer comprising high core bicomponent fibers and low core bicomponent fibers. Alternatively, the first layer can comprise high core bicomponent fibers and the second layer can comprise any suitable synthetic fibers. For example, and not limitation, the synthetic fibers can be eccentric bicomponent fibers having a core material selected from the polypropylene, poly (ethylene terephthalate), and combinations thereof.

In other particular embodiments, an airlaid nonwoven material can have at least three layers, including a first layer comprising high core bicomponent fibers and cellulose fibers, wherein the first layer is coated on at least a portion of its surface with a binder, a second layer comprising synthetic fibers, and a third layer comprising synthetic fibers. In certain aspects, such materials can be incorporated into acquisition materials. For example and not limitation, the acquisition materials can be used, along with an absorbent core, in various absorbent products.

In other particular embodiments, an airlaid nonwoven material can have at least three layers, including a first layer comprising synthetic fibers, a second layer comprising high core bicomponent fibers, and a third layer comprising cellulose fibers, wherein the third layer is coated on at least a portion of its surface with a binder. In certain embodiments, the second layer can further include cellulose fibers. As embodied herein, the material can optionally include an intermediate SAP layer comprising super absorbent polymer. In certain aspects, such materials can be incorporated into absorbent products as multifunctional, unitary structures.

In certain embodiments, the airlaid nonwoven material can have four or more layers. In such embodiments, at least one intermediate layer can contain high core bicomponent fibers. In particular embodiments, two or more intermediate layers can contain high core bicomponent fibers. Alternatively, the airlaid nonwoven material can have three or fewer layers. In certain embodiments, the airlaid nonwoven material does not contain cellulose fibers. In certain embodiments, at least one layer of the airlaid nonwoven material comprises a blend of high core bicomponent fibers and another type of synthetic fibers, such as low core bicomponent fibers.

The foregoing has outlined broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

4. BRIEF DESCRIPTION OF THE DRAWINGS

FIG. 1 provides a comparison of the stack heights of the samples of Example 3 after pressure.

Figure 2:
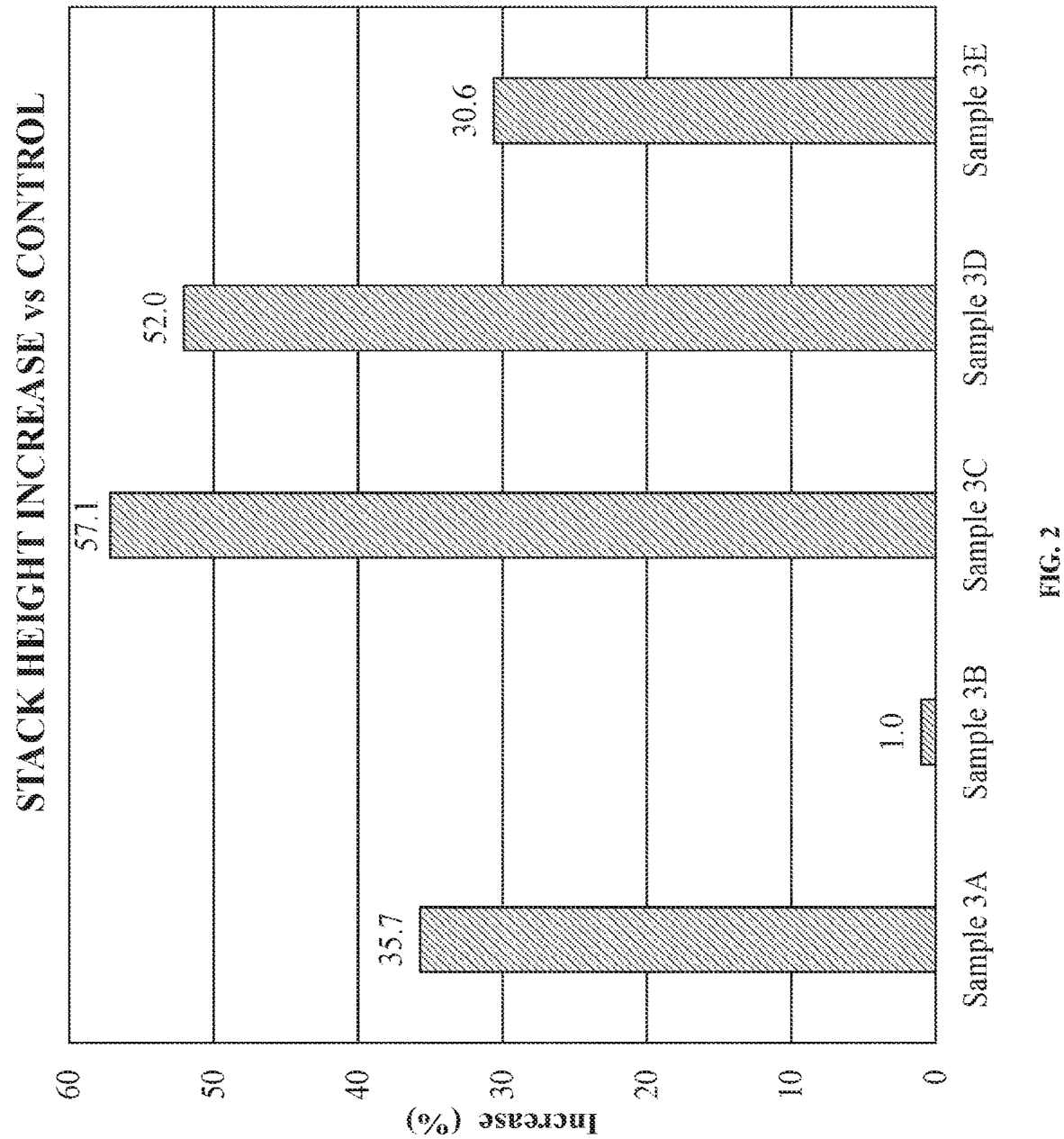

FIG. 2 compares the stack heights of nonwoven materials of the present disclosure with that of a control material, and provides the percent increase as compared to the control, in accordance with Example 3.

Figure 3:
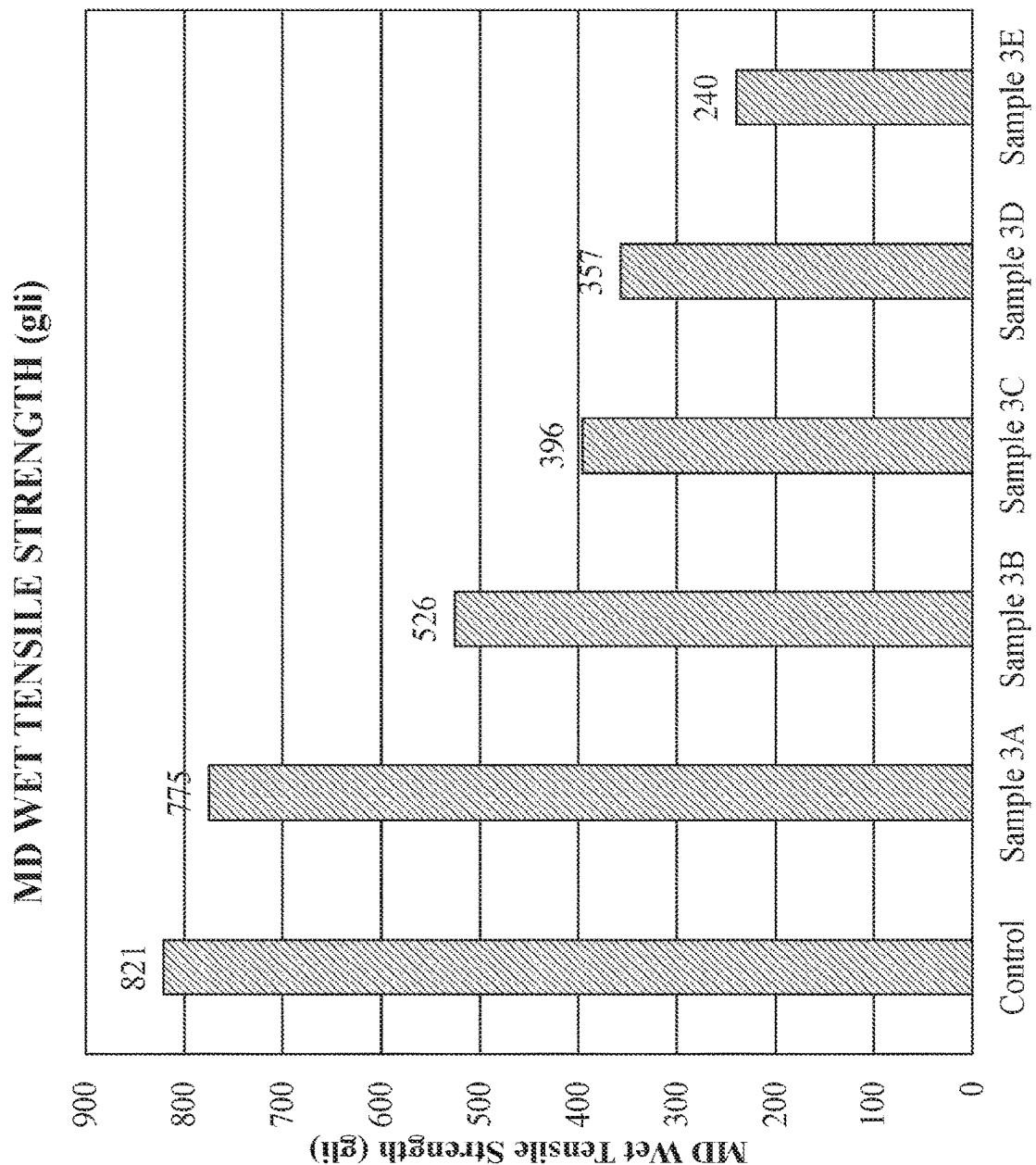

FIG. 3 provides a comparison of the machine-direction wet tensile strengths of the samples of Example 3.

Figure 4:
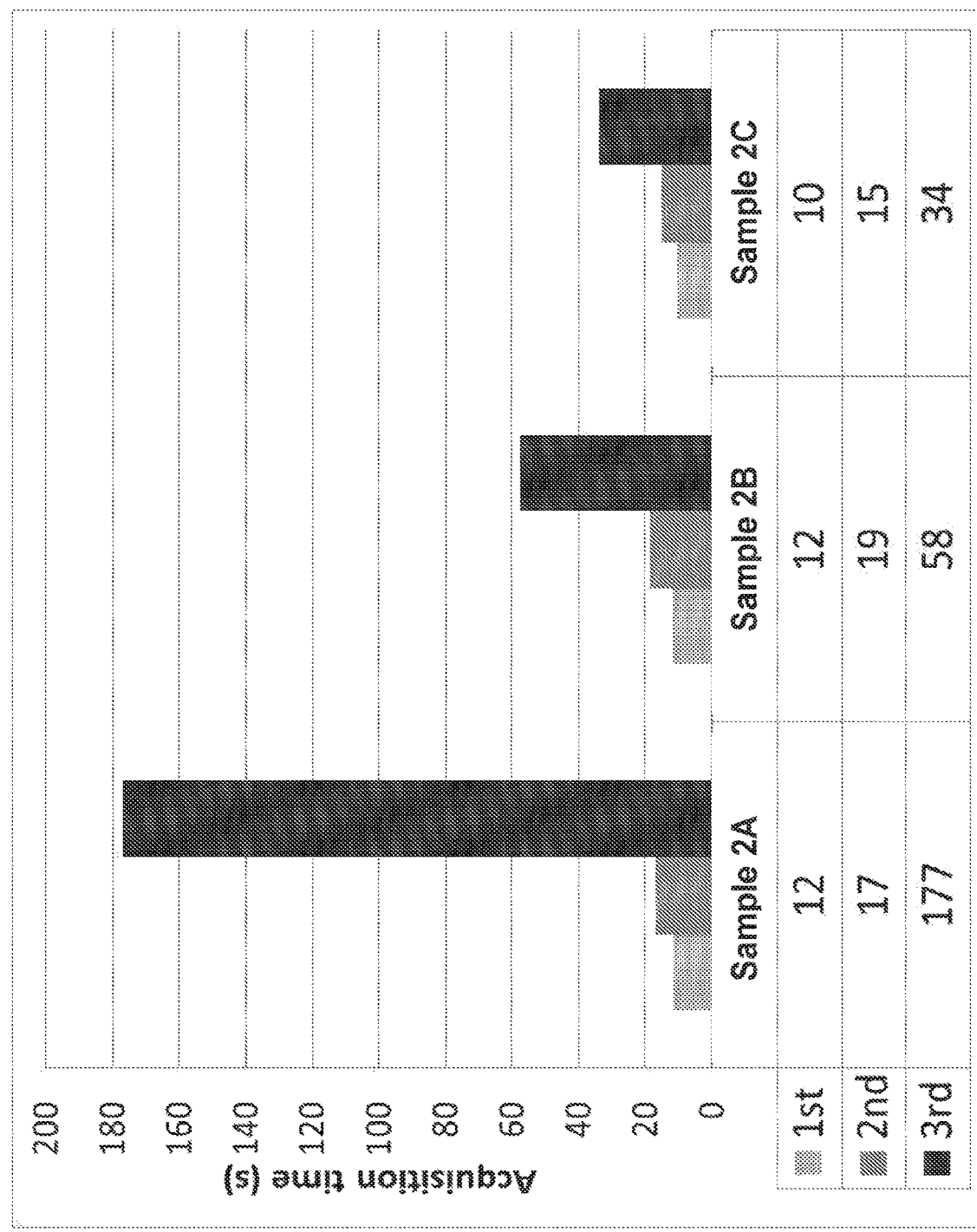

FIG. 4 provides the average acquisition times for Samples 4A-4C of Example 4.

Figure 5A:
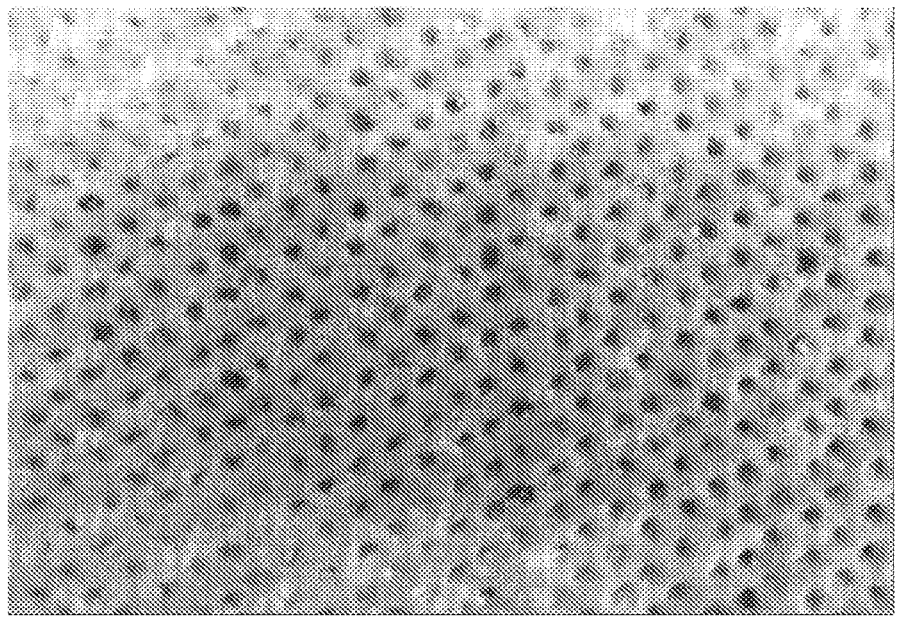

FIG. 5A provides a photograph of the pattern of Sample 5B of Example 5.

Figure 5B:
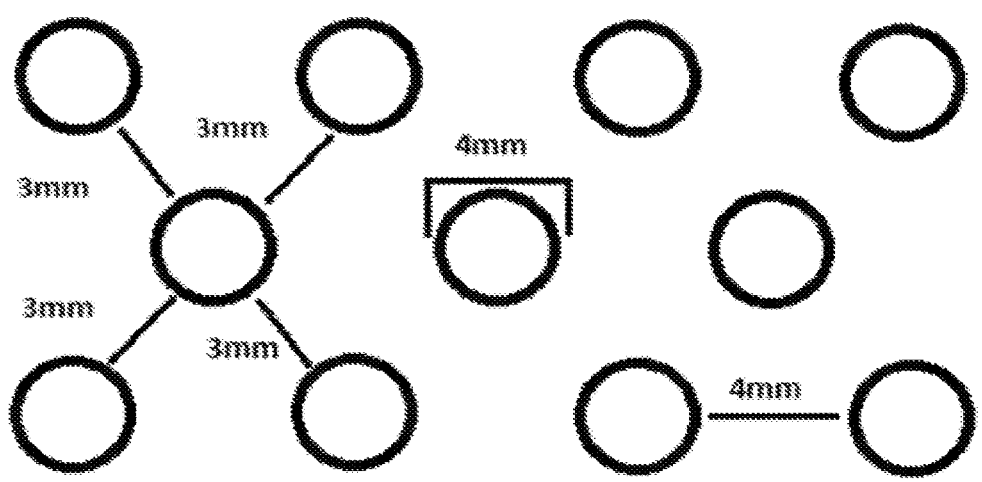

FIG. 5B provides a schematic representation, for illustrative purposes only, of the pattern of Sample 5B of Example 5.

Figure 6:
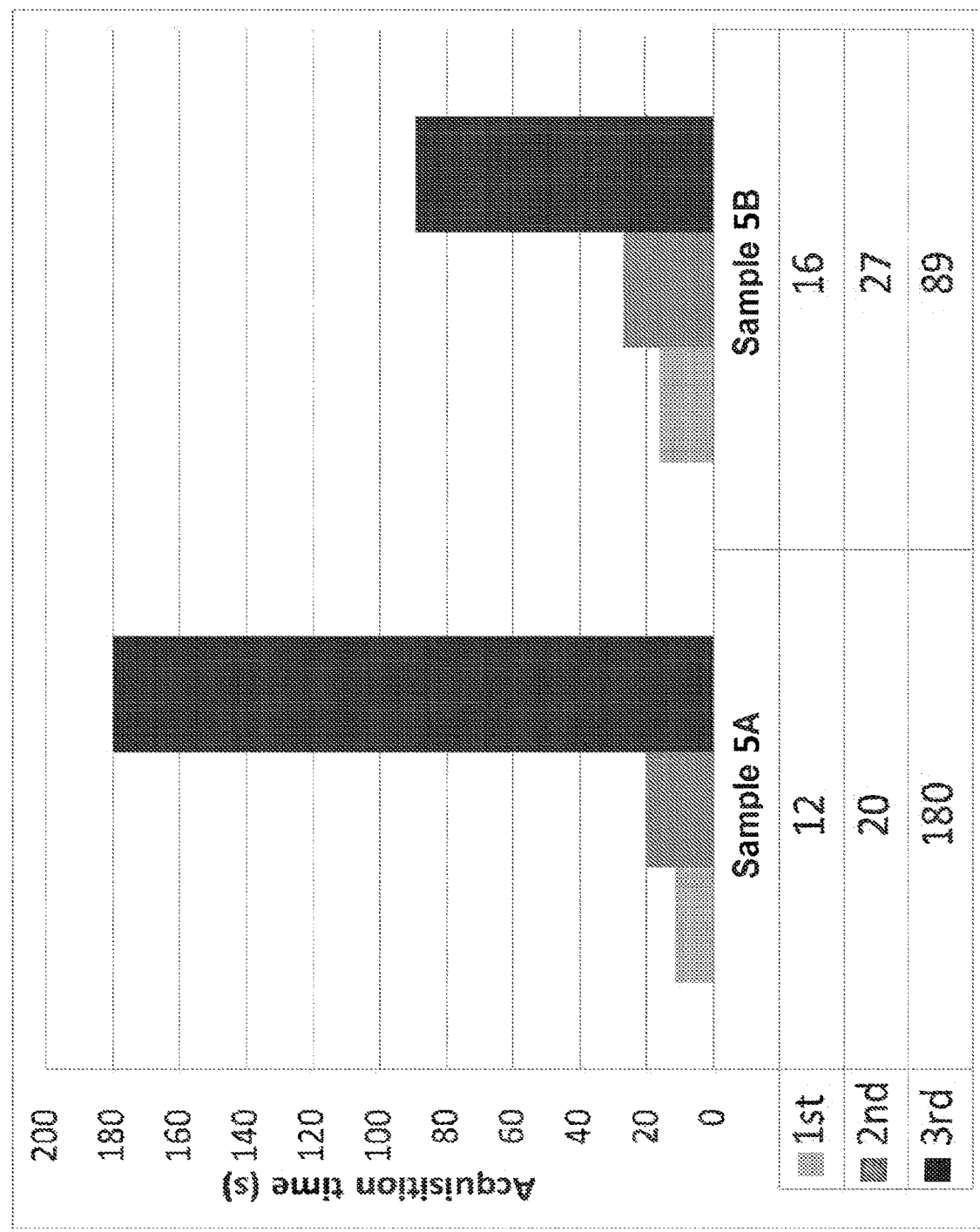

FIG. 6 provides the average acquisition times for Samples 5A-5B of Example 5.

Figure 7A:
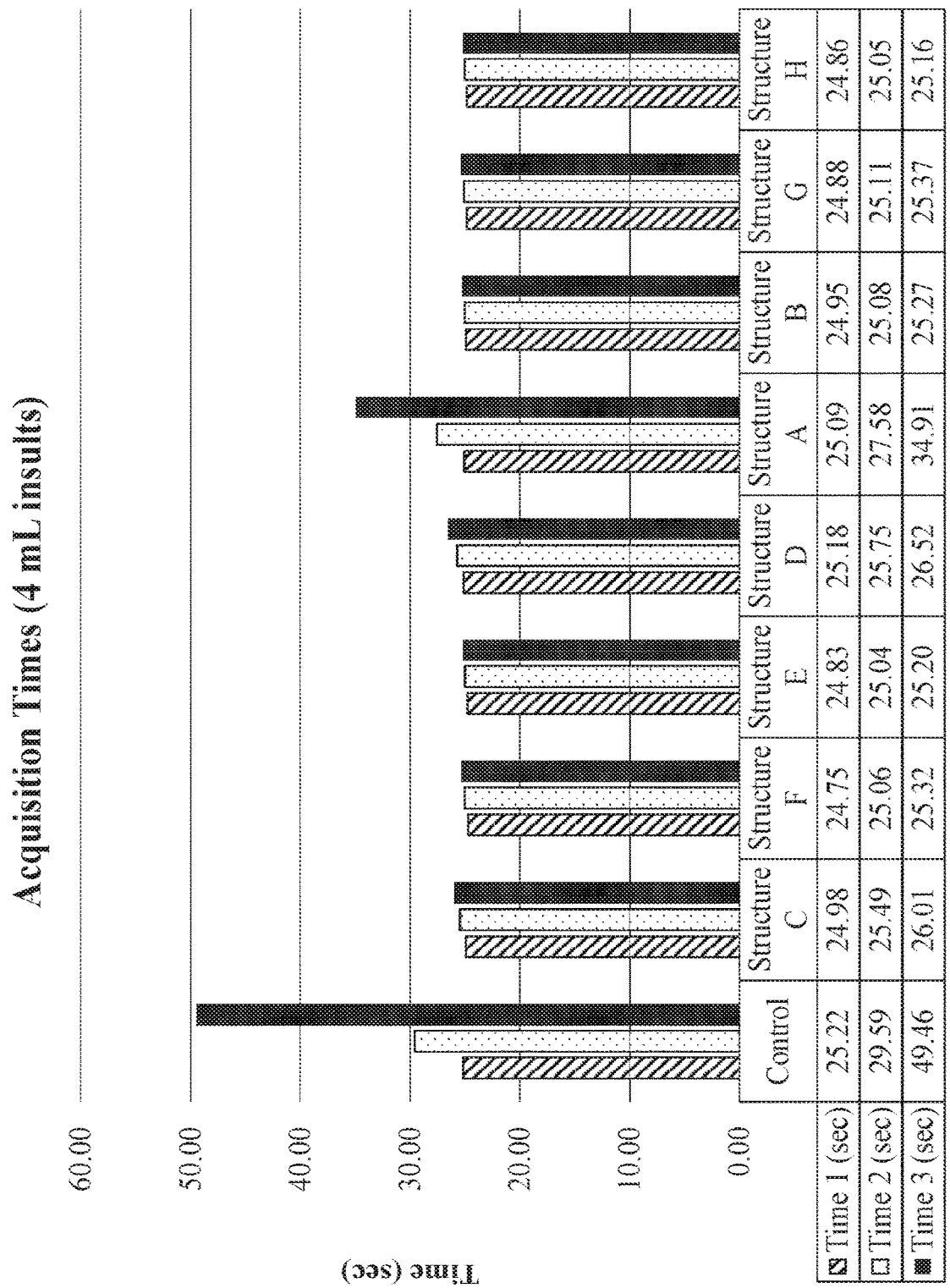
Figure 7B:
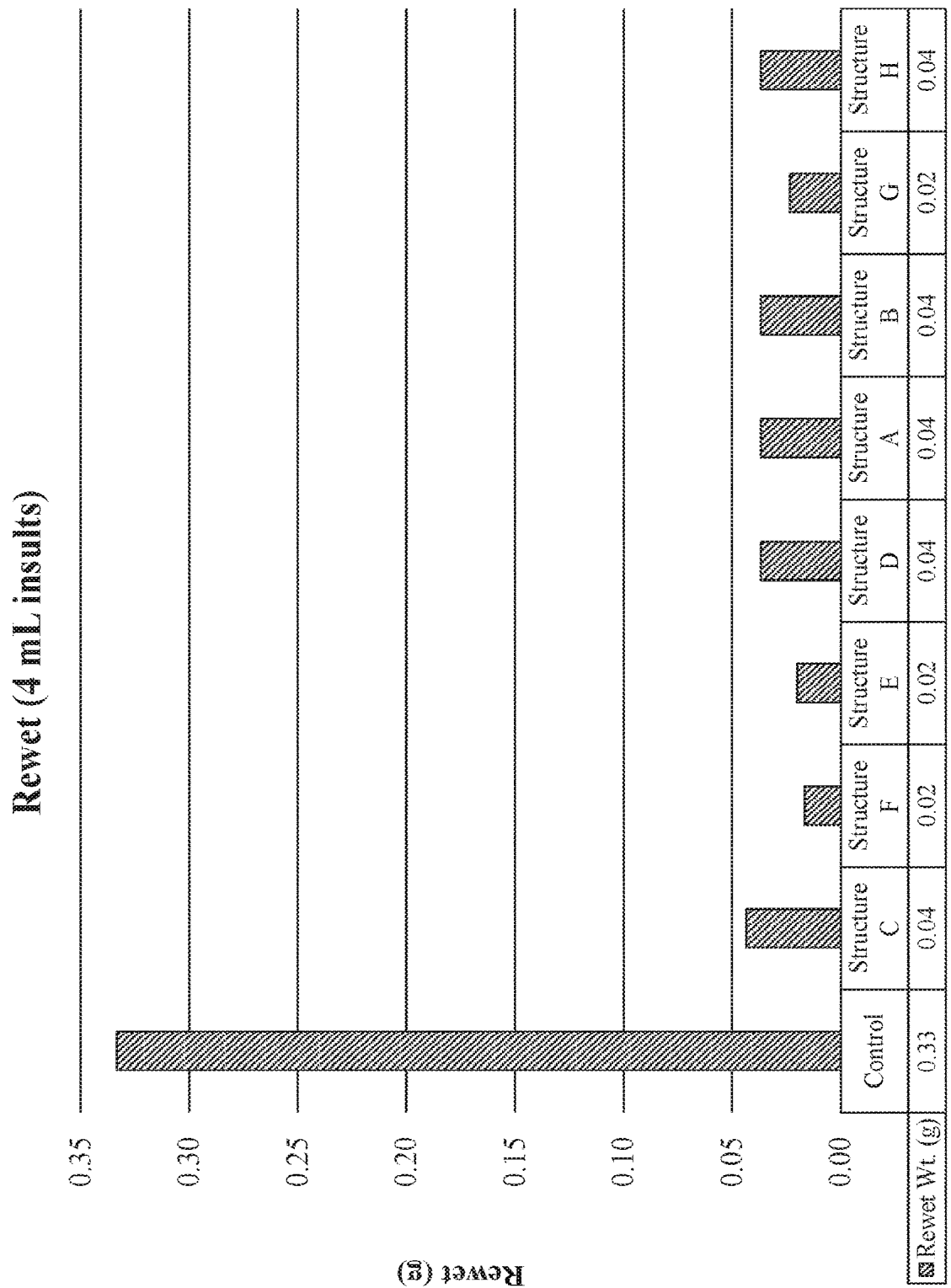
Figure 7C:
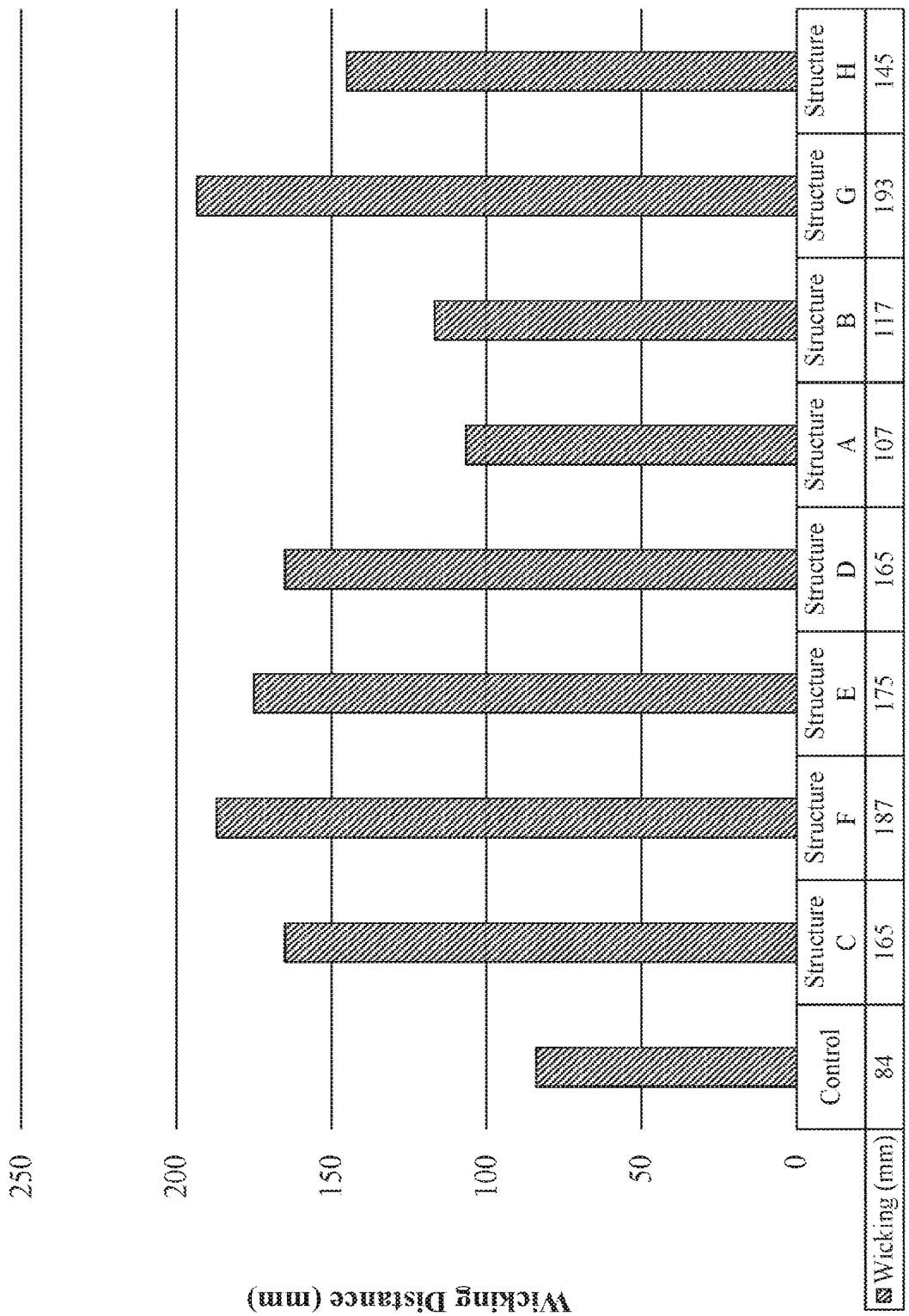

FIGS. 7A-7C provide the absorbency characteristics of Samples 6A-6H of Example 6 when tested with 4 mL insults. FIG. 7A provides the acquisition times, FIG. 7B provides the rewet weight, and FIG. 7C provides the wicking data for each sample and the Control.

Figure 8A:
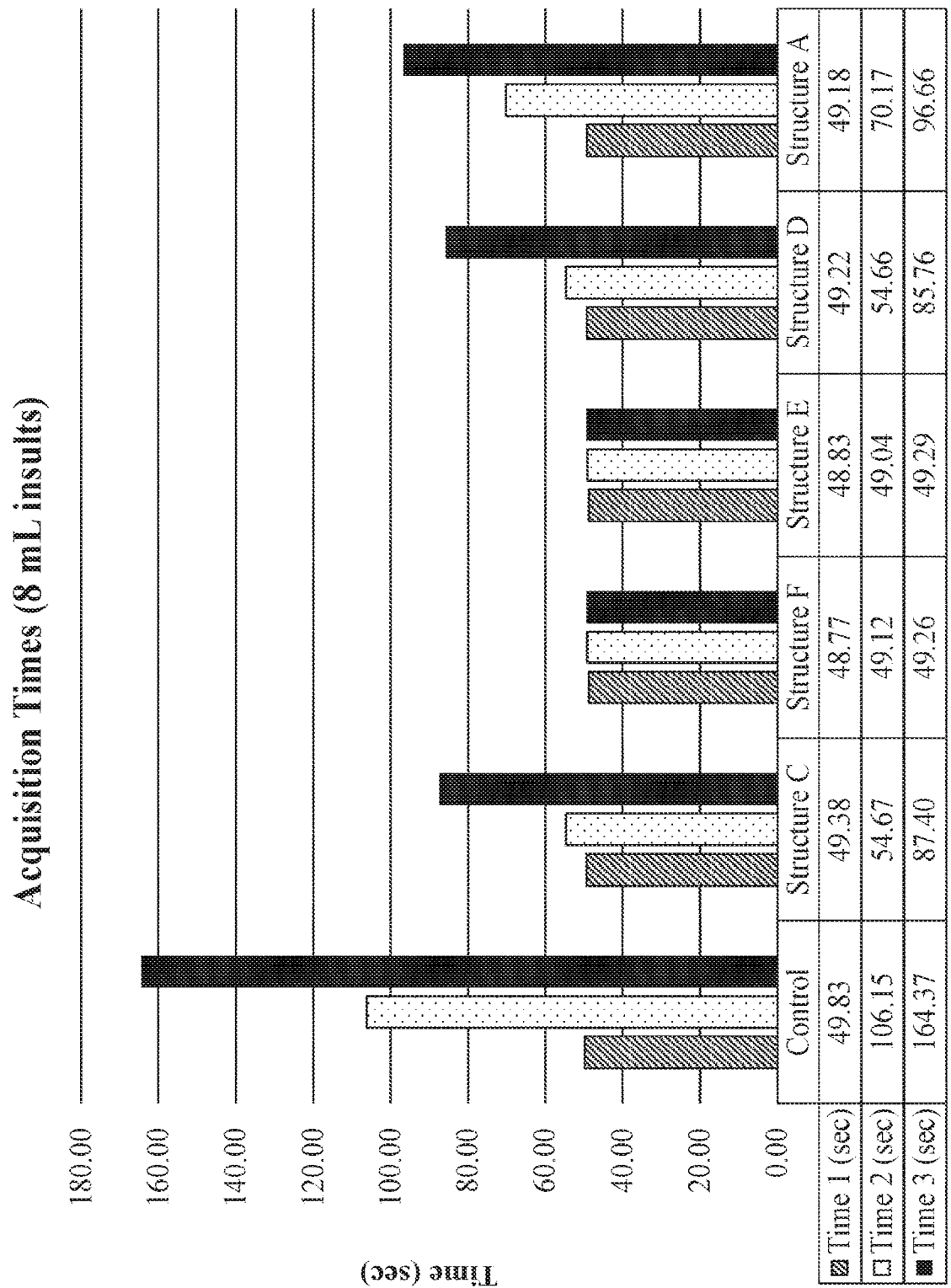
Figure 8C:
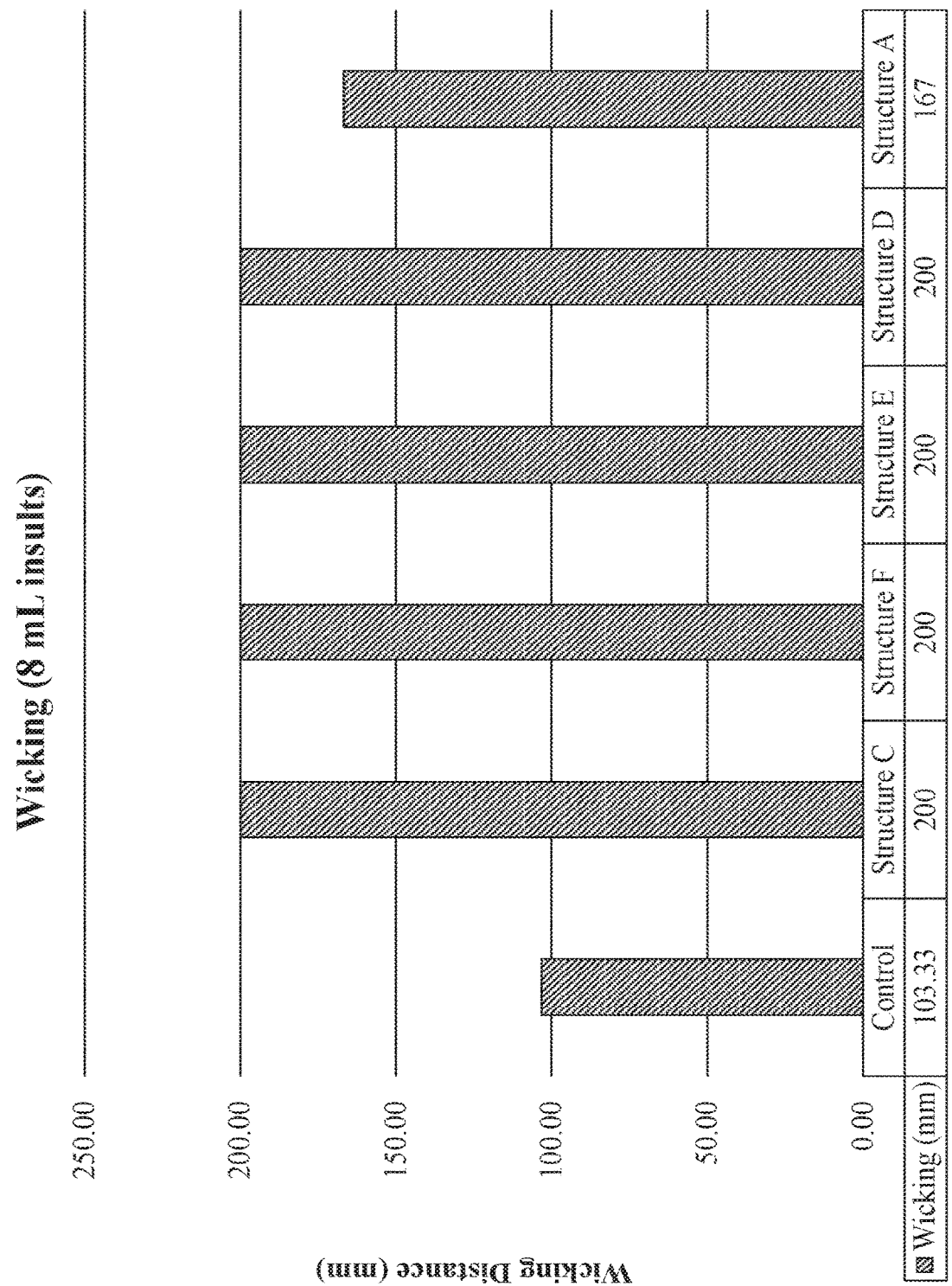

FIGS. 8A-8C provide the absorbency characteristics of Samples 6A and 6C-6F of Example 6 when tested with 8 mL insults. FIG. 8A provides the acquisition times, FIG. 8B provides the rewet weight, and FIG. 8C provides the wicking data for each sample and the Control.

Figure 9A:
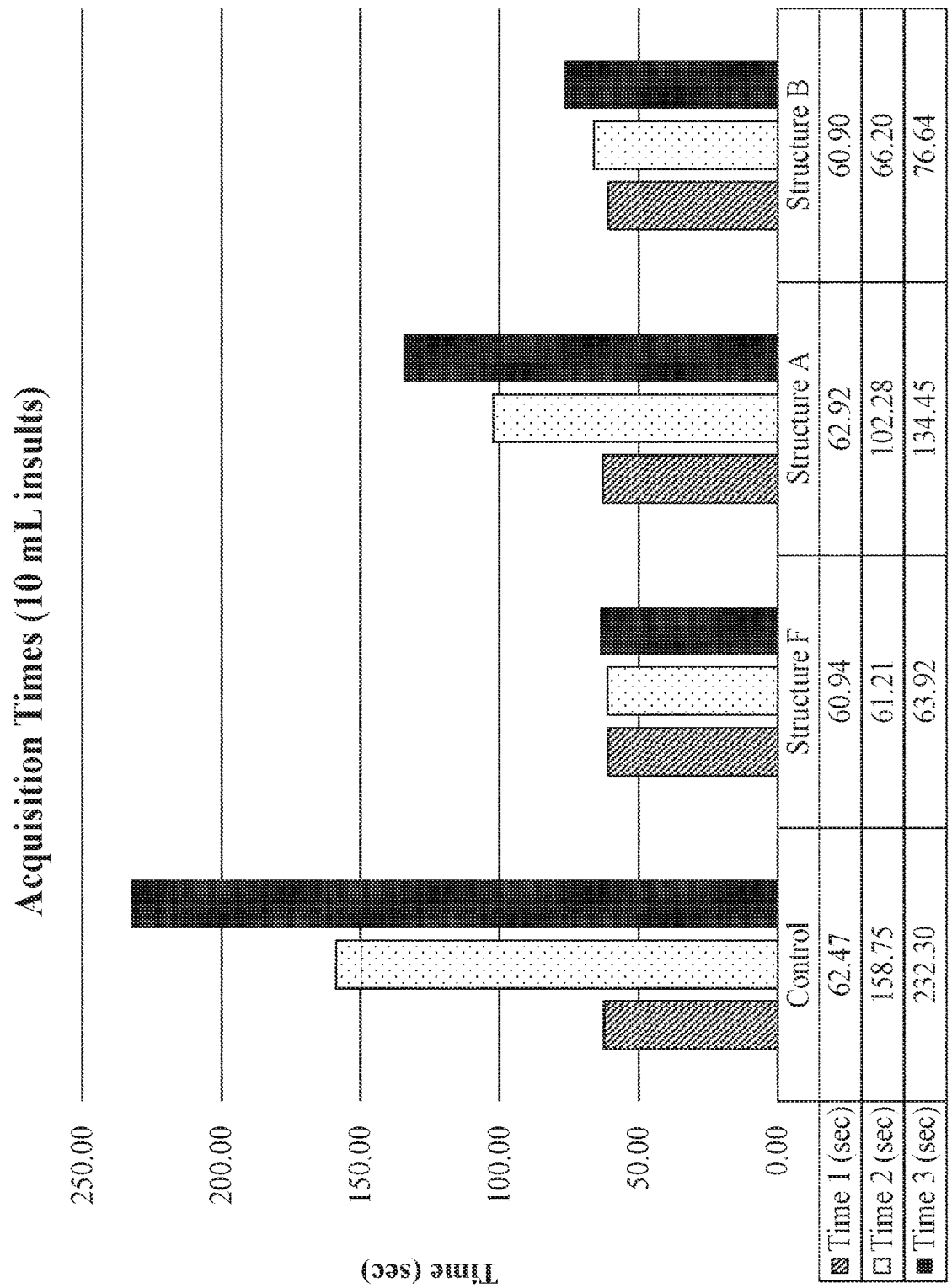
Figure 9B:
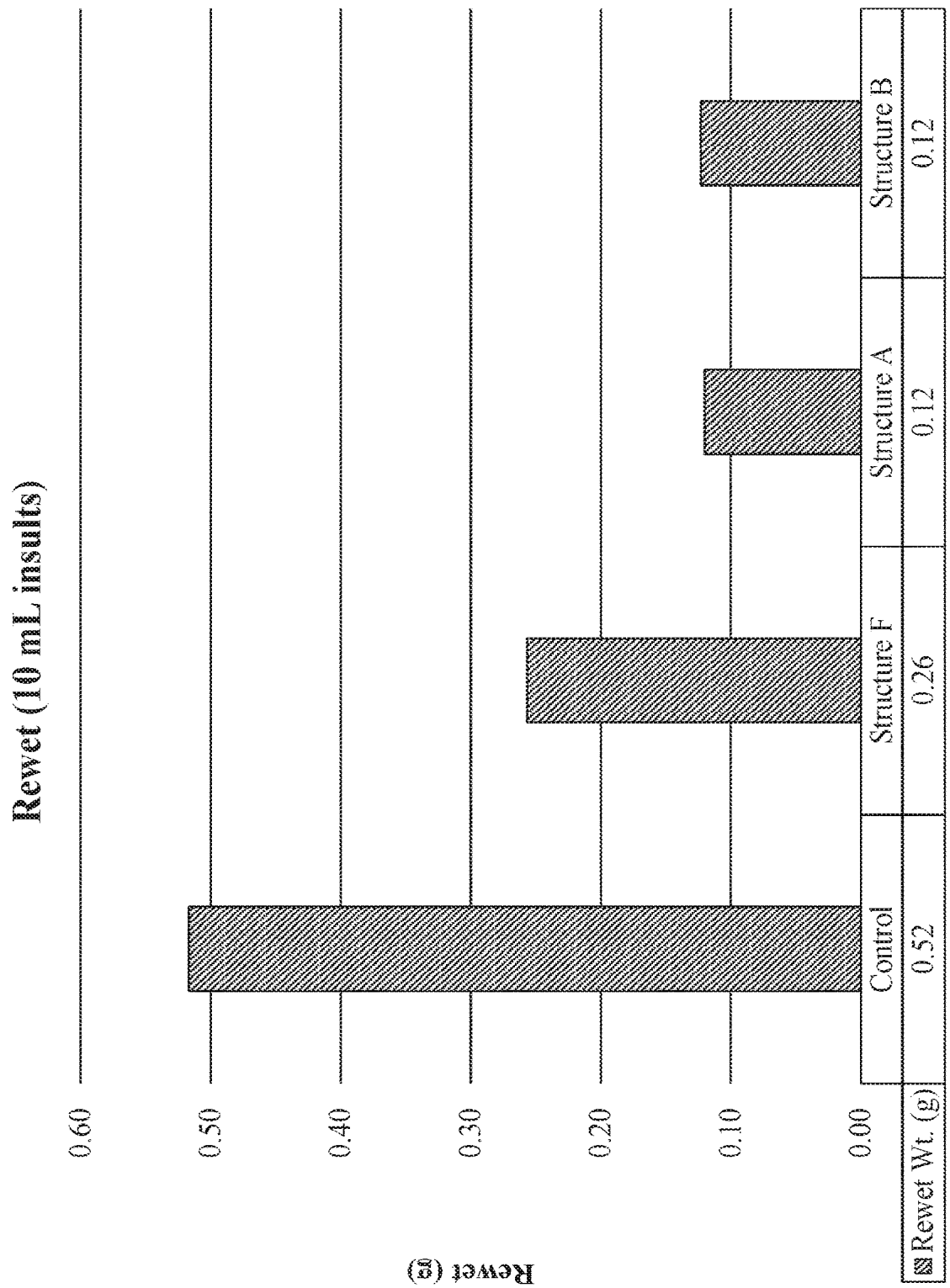
Figure 9C:
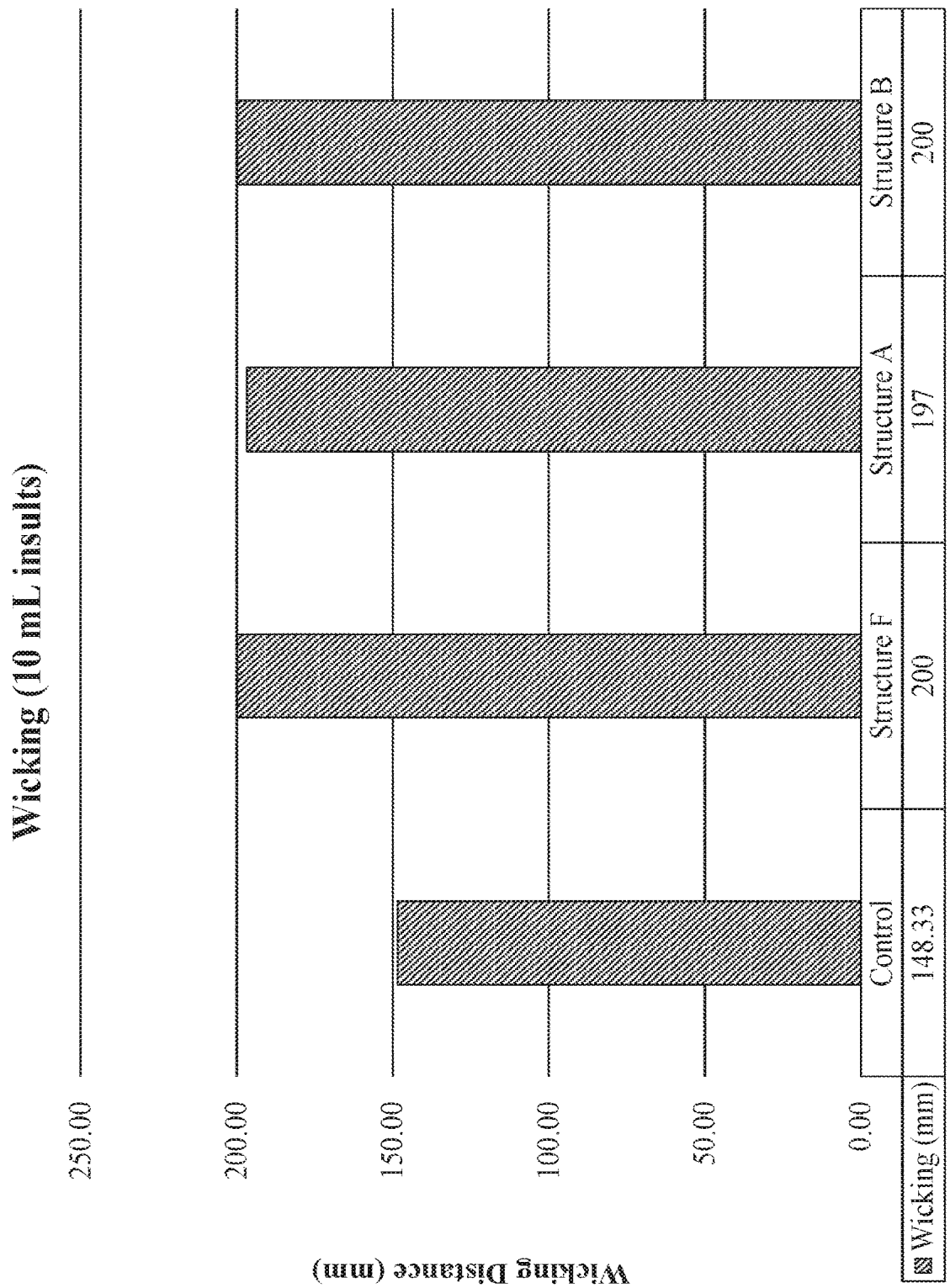

FIGS. 9A-9C provide the absorbency characteristics of Samples 6A, 6B, and 6F of Example 6 when tested with 10 mL insults. FIG. 9A provides the acquisition times, FIG. 9B provides the rewet weight, and FIG. 9C provides the wicking data for each sample and the Control.

Figure 10A:
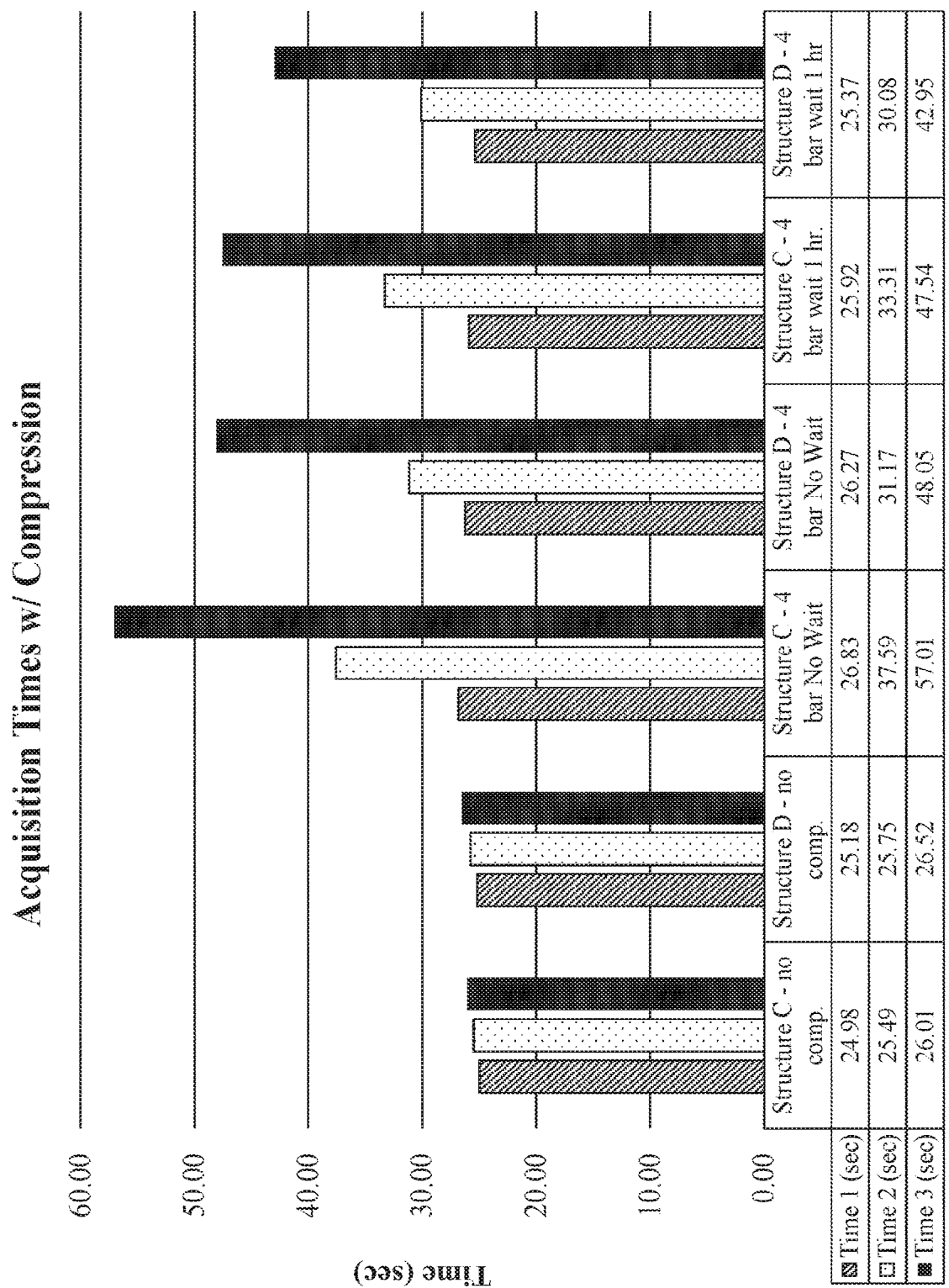
Figure 10B:
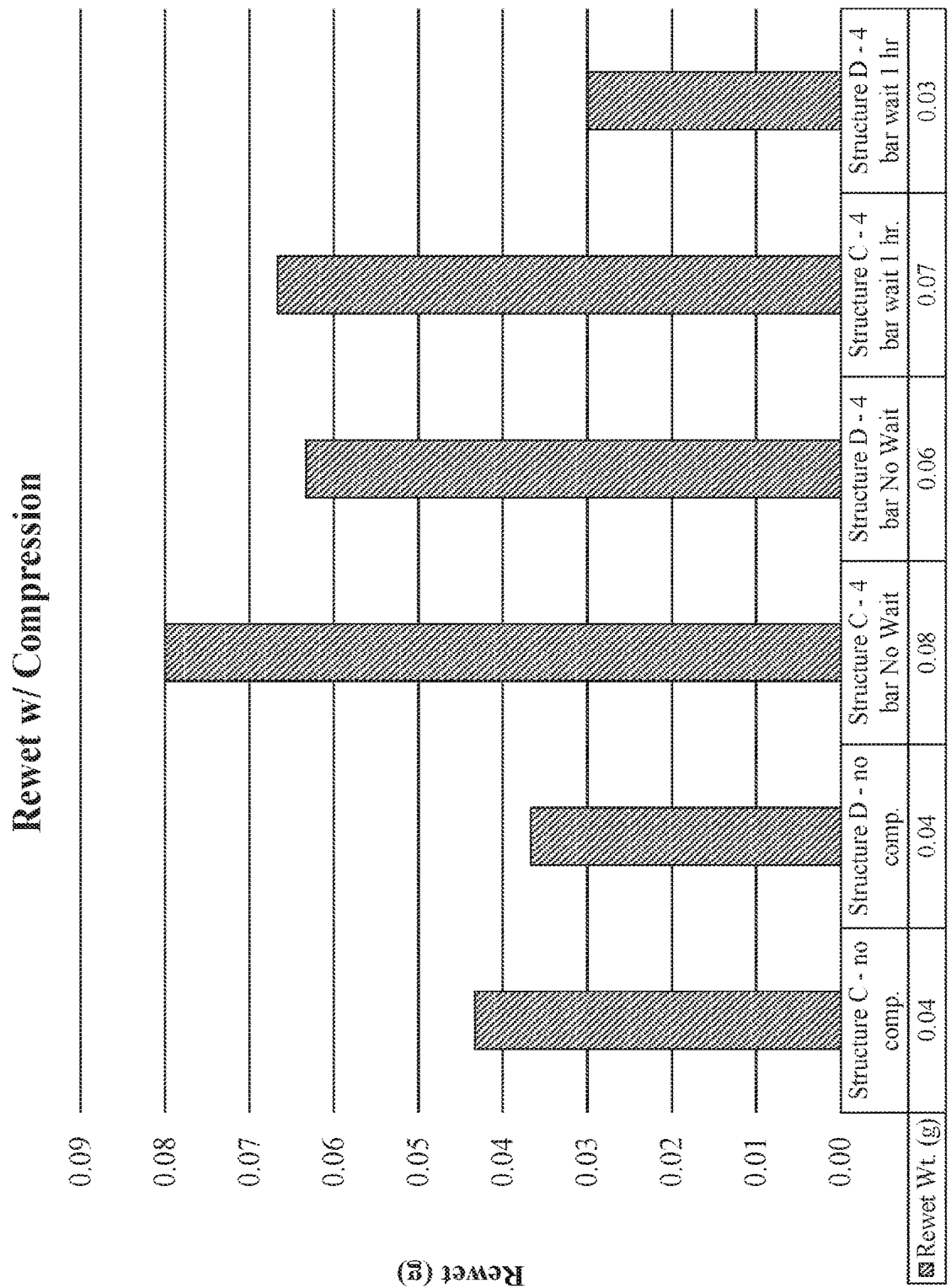
Figure 10C:
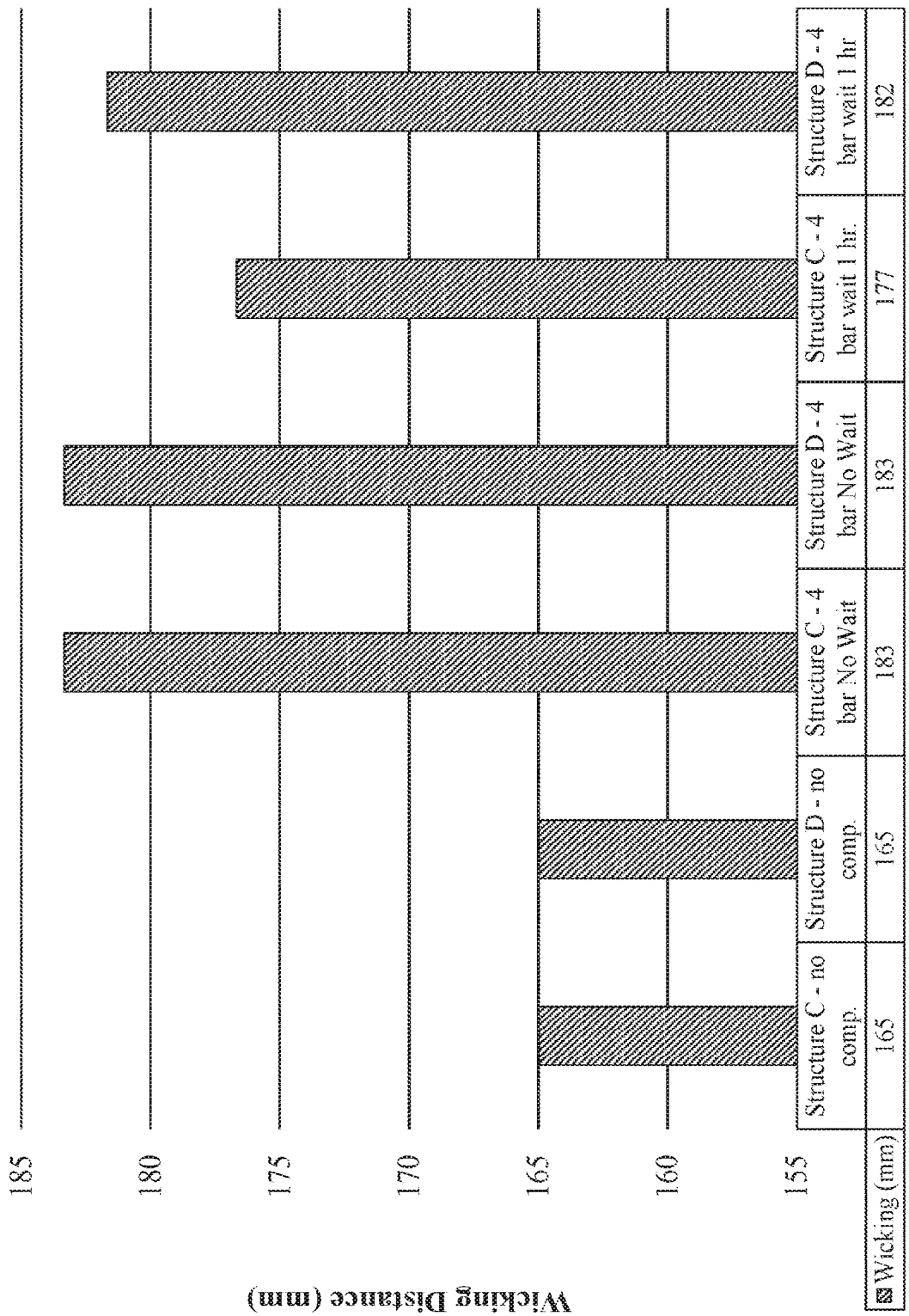

FIGS. 10A-10C provide the absorbency characteristics of Samples 6C and 6D of Example 6 when tested prior to compression, immediately after compression, and 1 hour after compression with 4 mL insults. FIG. 10A provides the acquisition times, FIG. 10B provides the rewet weight, and FIG. 10C provides the wicking data for each sample.

5. DETAILED DESCRIPTION

The presently disclosed subject matter provides for nonwoven materials containing high core bicomponent fibers, which can be used for a variety of applications. The presently disclosed subject matter also provides methods for making such materials. These and other aspects of the disclosed subject matter are discussed more in the detailed description and examples.

Definitions

The terms used in this specification generally have their ordinary meanings in the art, within the context of this subject matter and in the specific context where each term is used. Certain terms are defined below to provide additional guidance in describing the compositions and methods of the disclosed subject matter and how to make and use them.

As used in the specification and the appended claims, the singular forms "a," "an" and "the" include plural referents unless the context clearly dictates otherwise. Thus, for example, reference to "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to systems or processes, the term can mean within an order of magnitude, preferably within 5-fold, and more preferably within 2-fold, of a value.

As used herein, the term "weight percent" is meant to refer to either (i) the quantity by weight of a constituent/component in the material as a percentage of the weight of a layer of the material; or (ii) to the quantity by weight of a constituent/component in the material as a percentage of the weight of the final nonwoven material or product.

The term "basis weight" as used herein refers to the quantity by weight of a compound over a given area. Examples of the units of measure include grams per square meter as identified by the acronym "gsm".

As used herein, a "nonwoven" refers to a class of material, including but not limited to textiles or plastics. Nonwovens are sheet or web structures made of fiber, filaments, molten plastic, or plastic films bonded together mechanically, thermally, or chemically. A nonwoven is a fabric made directly from a web of fiber, without the yarn preparation necessary for weaving or knitting. In a nonwoven, the assembly of fibers is held together by one or more of the following: (1) by mechanical interlocking in a random web or mat; (2) by fusing of the fibers, as in the case of thermoplastic fibers; or (3) by bonding with a cementing medium such as a natural or synthetic resin.

As used herein, the term "cellulose" or "cellulosic" includes any material having cellulose as a major constituent, and specifically, comprising at least 50 percent by weight cellulose or a cellulose derivative. Thus, the term includes cotton, typical wood pulps, cellulose acetate, rayon, thermochemical wood pulp, chemical wood pulp, debonded chemical wood pulp, milkweed floss, microcrystalline cellulose, microfibrillated cellulose, and the like.

As used herein, the term "fiber" or "fibrous" refers to a particulate material wherein the length to diameter ratio of such particulate material is greater than about 10. Conversely, a "nonfiber" or "nonfibrous" material is meant to refer to a particulate material wherein the length to diameter ratio of such particulate matter is about 10 or less.

As used herein, the phrase "chemically modified," when used in reference to a fiber, means that the fiber has been treated with a polyvalent metal-containing compound to produce a fiber with a polyvalent metal-containing compound bound to it. It is not necessary that the compound chemically bond with the fibers, although it is preferred that the compound remain associated in close proximity with the fibers, by coating, adhering, precipitation, or any other mechanism such that it is not dislodged from the fibers during normal handling of the fibers. In particular, the compound can remain associated with the fibers even when wetted or washed with a liquid. For convenience, the association between the fiber and the compound may be referred to as the bond, and the compound may be said to be bound to the fiber.

As used herein, the phrase "high core bicomponent fibers" refers to bicomponent fibers having a core-sheath configuration, wherein the core comprises more than 50% of the fiber, by weight. Equivalently stated, it can be said that high core bicomponent fibers have a core to sheath ratio of greater than 1:1.

Fibers

The nonwoven materials of the presently disclosed subject matter comprises fibers, and at least a portion of the fibers are bicomponent fibers, specifically, bicomponent fibers having a core-sheath configuration and comprising more than 50% core by weight, i.e., "high core bicomponent fibers". The remaining portion of the fibers of the nonwoven materials can be natural, synthetic, or a mixture thereof.

Bicomponent Fibers

The presently disclosed subject matter contemplates the use of synthetic fibers, such as high core bicomponent fibers. Bicomponent fibers having a core and sheath are known in the art, but the present disclosure utilizes novel bicomponent fibers having a high core to sheath ratio that exceeds 1:1, i.e., the high core bicomponent fibers comprise more than 50% core by weight. Without being bound to a particular theory, it is believed that the high core bicomponent fibers can impart improved physical integrity, resiliency, and resistance to mechanical compression and/or tension to a nonwoven material. For example, the high core bicomponent fibers can impart these improved properties due to the increased volume of the core relative to the sheath.

As embodied herein, the high core bicomponent fibers can have a polyethylene sheath. The core of the high core bicomponent fibers can be made from a polymer with a melting point greater than about 200° C. and higher density than the polyethylene sheath. For example and not limitation, suitable core polymers include high melt point polyesters, such as poly(ethylene terephthalate) (PET), and polypropylene (PP). The core to sheath ratio of the high core bicomponent fibers can range from about 1:1 to about 2.5:1, or from about 1:1 to about 7:3, or from about 1.5:1 to about 7:3.

In certain embodiments, a high core bicomponent fiber can have a PET core and a polyethylene sheath in an eccentric configuration, wherein the PET core forms more than about 50% and no more than about 70% by weight of the fiber. For example, and not limitation, the PET core can form from about 60% to about 70% by weight of the fiber, and preferably, about 70% by weight of the fiber. In alternative embodiments, the high core bicomponent fibers can comprise a polypropylene core and a polyethylene sheath. In particular embodiments, such a high core bicomponent fiber can have a dtex of from about 1.7 dtex and a cut length of about 6 mm, although a person of skill in the art will appreciate that the bicomponent fiber can be formed with other thicknesses and cut lengths. For example and not limitation, the high core bicomponent fiber can have a dtex of from about 1.3 dtex to about 6.7 dtex, or from about 1.5 dtex to about 3.3 dtex, or from about 1.7 dtex to about 3.3 dtex. Additionally or alternatively, the high core bicomponent fiber can have a cut length of from about 4 mm to about 8 mm.

In addition to high core bicomponent fibers, the nonwoven material can further include any suitable additional bicomponent fibers, as known in the art. The additional bicomponent fibers can be conventional, commercially available fibers or can be low core bicomponent fibers, having a core to sheath ratio of less than 1:1, i.e., the low core bicomponent fibers comprise less than 50% core by weight. For example, suitable low core bicomponent fibers can comprise a PET core and a polyethylene sheath in an eccentric configuration and the PET core can form at least about 30% and less than about 50% by weight of the fiber, preferable from about 30% to about 40% by weight of the fiber, and more preferably about 30% by weight the fiber. In certain embodiments, a low core bicomponent fiber can impart improved strength to a nonwoven material, e.g., due to increased inter-fiber bonding due to the high volume of the sheath relative to the core.

However, many other varieties of bicomponent fibers are used in the manufacture of nonwoven materials, particularly those produced for use in airlaid techniques, and are suitable for use in the presently disclosed nonwoven materials. Various bicomponent fibers suitable for use in the presently disclosed subject matter are disclosed in U.S. Pat. Nos. 5,372,885 and 5,456,982, both of which are hereby incorporated by reference in their entireties. Examples of bicomponent fiber manufacturers include, but are not limited to, TREVIRA (Bobingen, Germany), Fiber Innovation Technologies (Johnson City, Tenn.) and ES Fiber Visions (Athens, Ga.).

The additional bicomponent fibers can also incorporate a variety of polymers as their core and sheath components. Bicomponent fibers that have a PE (polyethylene) or modified PE sheath typically have a PET (polyethylene terephthalate) or PP (polypropylene) core. In one embodiment, the bicomponent fibers have a core made of polypropylene and a sheath made of polyethylene. Alternatively or additionally, the bicomponent fibers can have a core made of polyester (e.g., PET) and a sheath made of polyethylene.

As embodied herein, the bicomponent fiber can be low staple fibers having a dtex from about 1.0 dtex to about 15.0 dtex, or from about 1.0 dtex to about 10.0 dtex, and more preferably no more than about 5.7 dtex. For example, the dtex of the bicomponent fiber can be about 1.5 dtex, about 1.7 dtex, about 2.0 dtex, about 2.2 dtex, about 3.0 dtex, about 3.3 dtex, about 5.0 dtex, or about 5.7 dtex. The length of the bicomponent fiber can be from about 2 mm to about 36 mm, preferably from about 3 mm to about 12 mm, more preferably from about 3 mm to about 10, even more preferably from about 4 mm to about 8 mm. In particular embodiments, the length of the bicomponent fiber is from about 4 mm to about 6 mm, or about 4 mm, or about 6 mm.

Bicomponent fibers are typically fabricated commercially by melt spinning. In this procedure, each molten polymer is extruded through a die, for example, a spinneret, with subsequent pulling of the molten polymer to move it away from the face of the spinneret. This is followed by solidification of the polymer by heat transfer to a surrounding fluid medium, for example chilled air, and taking up of the now solid filament. Non-limiting examples of additional steps after melt spinning can also include hot or cold drawing, heat treating, crimping and cutting. This overall manufacturing process is generally carried out as a discontinuous two-step process that first involves spinning of the filaments and their collection into a tow that comprises numerous filaments. During the spinning step, when molten polymer is pulled away from the face of the spinneret, some drawing of the filament does occur which can also be called the drawdown. This is followed by a second step where the spun fibers are drawn or stretched to increase molecular alignment and crystallinity and to give enhanced strength and other physical properties to the individual filaments. Subsequent steps can include, but are not limited to, heat setting, crimping and cutting of the filament into fibers. The drawing or stretching step can involve drawing the core of the bicomponent fiber, the sheath of the bicomponent fiber or both the core and the sheath of the bicomponent fiber depending on the materials from which the core and sheath are comprised as well as the conditions employed during the drawing or stretching process.

Bicomponent fibers can also be formed in a continuous process where the spinning and drawing are done in a continuous process. During the fiber manufacturing process it is desirable to add various materials to the fiber after the melt spinning step at various subsequent steps in the process. These materials can be referred to as "finish" and be comprised of active agents such as, but not limited to, lubricants and anti-static agents. The finish is typically delivered via an aqueous based solution or emulsion. Finishes can provide desirable properties for both the manufacturing of the bicomponent fiber and for the user of the fiber, for example in an airlaid or wetlaid process.

Numerous other processes are involved before, during and after the spinning and drawing steps and are disclosed in U.S. Pat. Nos. 4,950,541, 5,082,899, 5,126,199, 5,372,885, 5,456,982, 5,705,565, 2,861,319, 2,931,091, 2,989,798, 3,038,235, 3,081,490, 3,117,362, 3,121,254, 3,188,689, 3,237,245, 3,249,669, 3,457,342, 3,466,703, 3,469,279, 3,500,498, 3,585,685, 3,163,170, 3,692,423, 3,716,317, 3,778,208, 3,787,162, 3,814,561, 3,963,406, 3,992,499, 4,052,146, 4,251,200, 4,350,006, 4,370,114, 4,406,850, 4,445,833, 4,717,325, 4,743,189, 5,162,074, 5,256,050, 5,505,889, 5,582,913, and 6,670,035, all of which are hereby incorporated by reference in their entireties.

The presently disclosed subject matter can also include, but are not limited to, articles that contain bicomponent fibers that are partially drawn with varying degrees of draw or stretch, highly drawn bicomponent fibers and mixtures thereof. These can include, but are not limited to, a highly drawn polyester core bicomponent fiber with a variety of sheath materials, specifically including a polyethylene sheath such as TREVIRA-255 (Varde, Denmark) or a highly drawn polypropylene core bicomponent fiber with a variety of sheath materials, specifically including a polyethylene sheath such as ES FIBERVISIONS AL-Adhesion-C (Varde, Denmark). Additionally, TREVIRA T265 bicomponent fiber (Varde, Denmark), having a partially drawn core with a core made of polybutylene terephthalate (PBT) and a sheath made of polyethylene can be used. The use of both partially drawn and highly drawn bicomponent fibers in the same structure can be leveraged to meet specific physical and performance properties based on how they are incorporated into the structure.

The bicomponent fibers of the presently disclosed subject matter are not limited in scope to any specific polymers for either the core or the sheath as any partially drawn core bicomponent fiber can provide enhanced performance regarding elongation and strength. The degree to which the partially drawn bicomponent fibers are drawn is not limited in scope as different degrees of drawing will yield different enhancements in performance. The scope of the partially drawn bicomponent fibers encompasses fibers with various core sheath configurations including, but not limited to concentric, eccentric, side by side, islands in a sea, pie segments and other variations. The relative weight percentages of the core and sheath components of the total fiber can be varied. In addition, the scope of this subject matter covers the use of partially drawn homopolymers such as polyester, polypropylene, nylon, and other melt spinnable polymers.

The scope of this subject matter also covers multicomponent fibers that can have more than two polymers as part of the fiber structure.

Other Synthetic Fibers

Other synthetic fibers suitable for use in various embodiments as fibers or as bicomponent binder fibers include, but are not limited to, fibers made from various polymers including, by way of example and not by limitation, acrylic, polyamides (including, but not limited to, Nylon 6, Nylon 6/6, Nylon 12, polyaspartic acid, polyglutamic acid), polyamines, polyimides, polyacrylics (including, but not limited to, polyacrylamide, polyacrylonitrile, esters of methacrylic acid and acrylic acid), polycarbonates (including, but not limited to, polybisphenol A carbonate, polypropylene carbonate), polydienes (including, but not limited to, polybutadiene, polyisoprene, polynorbornene), polyepoxides, polyesters (including, but not limited to, polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate), polyethers (including, but not limited to, polyethylene glycol (polyethylene oxide), polybutylene glycol, polypropylene oxide, polyoxymethylene (paraformaldehyde), polytetramethylene ether (polytetrahydrofuran), polyepichlorohydrin), polyfluorocarbons, formaldehyde polymers (including, but not limited to, urea-formaldehyde, melamine-formaldehyde, phenol formaldehyde), natural polymers (including, but not limited to, cellulosics, chitosans, lignins, waxes), polyolefins (including, but not limited to, polyethylene, polypropylene, polybutylene, polybutene, polyoctene), polyphenylenes (including, but not limited to, polyphenylene oxide, polyphenylene sulfide, polyphenylene ether sulfone), silicon containing polymers (including, but not limited to, polydimethyl siloxane, polycarbomethyl silane), polyurethanes, polyvinyls (including, but not limited to, polyvinyl butyral, polyvinyl alcohol, esters and ethers of polyvinyl alcohol, polyvinyl acetate, polystyrene, polymethylstyrene, polyvinyl chloride, polyvinyl pryrrolidone, polymethyl vinyl ether, polyethyl vinyl ether, polyvinyl methyl ketone), polyacetals, polyarylates, and copolymers (including, but not limited to, polyethylene-co-vinyl acetate, polyethylene-co-acrylic acid, polybutylene terephthalate-co-polyethylene terephthalate, polylauryllactam-block-polytetrahydrofuran), polybutylene succinate and polylactic acid based polymers. In certain embodiments, these polymer materials can be used in a monocomponent fiber. Alternatively, two or more polymer materials can be used together in a bicomponent fiber, e.g., a high core bicomponent fiber or a low core bicomponent fiber.

Cellulose Fibers

Any cellulose fibers known in the art, including cellulose fibers of any natural origin, such as those derived from wood pulp or regenerated cellulose, can be used in a cellulose fiber layer. In certain embodiment, cellulose fibers include, but are not limited to, digested fibers, such as kraft, prehydrolyzed kraft, soda, sulfite, chemi-thermal mechanical, and thermo-mechanical treated fibers, derived from softwood, hardwood or cotton linters. In other embodiments, cellulose fibers include, but are not limited to, kraft digested fibers, including prehydrolyzed kraft digested fibers. Non-limiting examples of cellulose fibers suitable for use in this subject matter are the cellulose fibers derived from softwoods, such as pines, firs, and spruces. Other suitable cellulose fibers include, but are not limited to, those derived from Esparto grass, bagasse, kemp, flax, hemp, kenaf, and other lignaceous and cellulosic fiber sources. Suitable cellulose fibers include, but are not limited to, bleached Kraft southern pine fibers sold under the trademark FOLEY FLUFFS® (available from GP Cellulose).

The nonwoven material of the disclosed subject matter can also include, but is not limited to, a commercially available bright fluff pulp including, but not limited to, southern softwood fluff pulp (such as Treated FOLEY FLUFFS® or Golden Isles® 4723 from GP Cellulose), northern softwood sulfite pulp (such as T 730 from Weyerhaeuser), or hardwood pulp (such as eucalyptus). While certain pulps may be preferred based on a variety of factors, any cellulosic fluff pulp or mixtures thereof can be used. In certain embodiments, wood cellulose, cotton linter pulp, chemically modified cellulose such as crosslinked cellulose fibers and highly purified cellulose fibers can be used. Non-limiting examples of additional pulps are FOLEY FLUFFS® FFTAS (also known as FFTAS or GP Cellulose FFT-AS pulp), and WEYCO CF401.

In certain embodiments, fine fibers, such as certain hardwood fibers can be used. Certain non-limiting examples of such fine fibers, with sample properties as obtained by Kajaani analysis, are provided in Table 1.

the polyvalent metal-containing compound, and preferably with from about 3 weight percent to about 8 weight percent of the polyvalent cation-containing compound, based on the dry weight of the untreated fiber.

Any polyvalent metal salt including transition metal salts may be used, provided that the compound is capable of increasing the stability of the cellulose fiber in an alkaline environment. Examples of suitable polyvalent metals include beryllium, magnesium, calcium, strontium, barium, titanium, zirconium, vanadium, chromium, molybdenum, tungsten, manganese, iron, cobalt, nickel, copper, zinc, aluminum and tin. Preferred ions include aluminum, iron and tin. The preferred metal ions have oxidation states of +3 or +4. In certain embodiments, the polyvalent metal is aluminum. Any salt containing the polyvalent metal ion may be employed. Examples of suitable inorganic salts of the above metals include chlorides, nitrates, sulfates, borates, bromides, iodides, fluorides, nitrides, perchlorates, phosphates, hydroxides, sulfides, carbonates, bicarbonates, oxides, alkoxides phenoxides, phosphites, and hypophosphites. Examples of suitable organic salts of the above metals include formates, acetates, butyrates, hexanoates, adipates, citrates, lactates, oxalates, propionates, salicylates, glycinates, tartrates, glycolates, sulfonates, phosphonates, glutamates, octanoates, benzoates, gluconates, maleates, succinates, and 4,5-dihydroxy-benzene-1,3-disulfonates. In

TABLE 1

| Sample | L. Wt. Avg. (0.25-7.60 mm) | L. Wt. Avg. (0.00-7.60 mm) | % Fines Wt. Avg. | % Fines (n) | Fiber Width (μm) | Kajaani Curl % | Kink (1/m) |
|---|---|---|---|---|---|---|---|
| Stora LKC | 2.46 | 2.43 | 1.22 | 11.83 | 23.4 | 24.7 | 1300 |
| Biobright FSC | 1.92 | 1.86 | 3.25 | 21.17 | 18.9 | 20.4 | 1350 |
| Stora EF | 2.24 | 2.17 | 3.57 | 27.37 | 22.2 | 22.9 | 1382 |
| Biobright TCF | 2.02 | 1.96 | 3.33 | 22.55 | 18.6 | 22.7 | 1516 |
| Steinfurt Domtar | 2.59 | 2.54 | 1.88 | 18.46 | 24.6 | 24.0 | 1455 |
| Domtar Ashdown Softwood | 2.56 | 2.50 | 2.35 | 21.09 | 24.2 | 23.2 | 1345 |
| *Eucalyptus* | 0.83 | 0.81 | 2.07 | 9.32 | 13.1 | 15.4 | 1857 |
| GP-4723 | 2.85 | 2.79 | 2.31 | 23.26 | 25.5 | 22.4 | 1080 |
| FFLE+ | 2.86 | 2.83 | 1.28 | 13.99 | 26.8 | 21.2 | 795 |
| GI-4725 | 2.84 | 2.78 | 2.40 | 23.86 | 25.6 | 20.9 | 803 |
| GI-4757 | 2.79 | 2.76 | 1.00 | 12.29 | 25.9 | 25.5 | 1411 |

Chemically Modified Cellulose Fibers

The presently disclosed subject matter contemplates the use of cellulose-based fibers that are chemically modified. As embodied herein, the cellulose fibers can be chemically treated with a compound comprising a polyvalent metal ion, e.g., a polyvalent cation. Such chemically modified fibers are described, for the purpose of illustration and not limitation, in U.S. Pat. Nos. 6,562,743 and 8,946,100, the contents of which are hereby incorporated by reference in their entireties. The chemically modified cellulose fibers can optionally be associated with a weak acid. For example, suitable modified cellulose fibers include aluminum-modified FFLE+ fibers from GP Cellulose.

The chemically modified cellulose fiber can be treated with from about 0.1 weight percent to about 20 weight percent of the polyvalent cation-containing compound, based on the dry weight of the untreated fiber, desirably with from about 2 weight percent to about 12 weight percent of addition to the polyvalent metal salts, other compounds such as complexes of the above salts include amines, ethylenediaminetetra-acetic acid (EDTA), diethylenetriaminepenta-acetic acid (DIPA), nitrilotri-acetic acid (NTA), 2,4-pentanedione, and ammonia may be used. In certain embodiments, the polyvalent metal salt is aluminum chloride, aluminum hydroxide, or aluminum sulfate. Alum is an aluminum sulfate salt which is soluble in water. In an aqueous slurry of cellulose, some of the alum will penetrate the fiber cell wall, but since the concentration of ions is low, most of the dissolved aluminum salt will be outside the fiber. When the pH is adjusted to precipitate aluminum hydroxide, most of the precipitate adheres to the fiber surface.

In certain embodiments, the chemically modified cellulose fiber has an acid bound or otherwise associated with it. A variety of suitable acids may be employed, although the acid preferably should have a low volatility. In certain embodiments, the acid is a weak acid.

For example, and not limitation, suitable acids include inorganic acids such as sodium bisulfate, sodium dihydrogen phosphate and disodium hydrogen phosphate, and organic acids such as formic, acetic, aspartic, propionic, butyric, hexanoic, benzoic, gluconic, oxalic, malonic, succinic, glutaric, tartaric, maleic, malic, phthallic, sulfonic, phosphonic, salicylic, glycolic, citric, butanetetracarboxylic acid (BTCA), octanoic, polyacrylic, polysulfonic, polymaleic, and lignosulfonic acids, as well as hydrolyzed-polyacrylamide and CMC (carboxymethylcellulose). Among the carboxylic acids, acids with two carboxyl groups are preferred, and acids with three carboxyl groups are more preferred. In certain embodiments, the acid is citric acid.

In general, the amount of acid employed can depend on the acidity and the molecular weight of the acid. In certain embodiments, the acid comprises from about 0.5 weight percent of the fibers to about 10 weight percent of the fibers. As used herein, the "weight percent of the fibers" refers to the weight percent of dry fiber treated with the polyvalent metal containing compound, i.e., based on the dry weight of the treated fibers. For example, in certain embodiments, the acid is citric acid in an amount of from about 0.5 weight percent to about 3 weight percent of the fibers. A preferred combination is an aluminum-containing compound and citric acid. For the chemically treated fibers of this aspect of this invention, it is desirable that the weak acid content of the chemically treated fibers is from about 0.5 weight percent to about 10 weight percent based on the dry weight of the treated fibers, more desirably, from about 0.5 weight percent to about 5 weight percent based on the dry weight of the treated fibers, and, preferably, from about 0.5 weight percent to about 3 weight percent based on the dry weight of the treated fibers.

Alternatively, in certain embodiments, a buffer salt can be used instead of a weak acid in combination with the polyvalent metal-containing compound. Any buffer salt that in water would provide a solution having a pH of less than about 7 is suitable. For example, and not limitation, suitable buffer salts include sodium acetate, sodium oxalate, sodium tartrate, sodium phthalate, sodium dihydrogen phosphate, disodium hydrogen phosphate and sodium borate. Buffer salts may be used in combination with their acids in a combination that in water would provide a solution having a pH of less than about 7, for example, oxalic acid/sodium oxalate, tartaric acid/sodium tartrate, sodium phthalate/phthalic acid, and sodium dihydrogen phosphate/disodium hydrogen phosphate.

In a further variation, the polyvalent metal-containing compound can be used in combination with an insoluble metal hydroxide, such as, for example, magnesium hydroxide, or in combination with one or more alkali stable anti-oxidant chemicals or alkali stable reducing agents that would inhibit fiber degradation in an alkaline oxygen environment. Examples include inorganic chemicals such as sodium sulfite, and organic chemicals such as hydroquinone.

For the chemically modified cellulose fibers, it is desirable that the buffer salt content, the buffer salt weak acid combination content, the insoluble metal hydroxide content and/or the antioxidant content of the chemically treated fibers is from about 0.5 weight percent to about 10 weight percent based on the dry weight of the treated fibers, more desirably, from about 0.5 weight percent to about 5 weight percent based on the dry weight of the treated fibers, and, preferably, from about 0.5 weight percent to about 3 weight percent based on the dry weight of the treated fibers.

In certain embodiments, reducing agents can be applied to the modified cellulose fibers to maintain desired levels of fiber brightness, by reducing brightness reversion. The addition of acidic substances may cause browning of fibers when heated during processing of webs containing the fibers. Reducing agents counter the browning of the fibers. The reducing agent can also bond to the fibers. Suitable reducing agents include sodium hypophosphite, sodium bisulfite, and mixtures thereof.

The fibers suitable for use in the practice of this invention may be treated in a variety of ways to provide the polyvalent metal ion-containing compound in close association with the fibers. A preferred method is to introduce the compound in solution with the fibers in slurry form and cause the compound to precipitate onto the surface of the fibers. Alternatively, the fibers may be sprayed with the compound in aqueous or non-aqueous solution or suspension. The fibers may be treated while in an individualized state, or in the form of a web. For example, the compound may be applied directly onto the fibers in powder or other physical form. Whatever method is used, however, it is preferred that the compound remain bound to the fibers, such that the compound is not dislodged during normal physical handling of the fiber before contact of the fiber with liquid.

In a preferred embodiment, the treated fibers of the present invention are made from cellulose fiber known as FOLEY FLUFFS® from GP Cellulose. The pulp is slurried, the pH is adjusted to about 4.0, and aluminum sulfate ($Al_2(SO_4)_3$) in aqueous solution is added to the slurry. The slurry is stirred and the consistency reduced. Under agitation, the pH of the slurry is increased to approximately 5.7. The fibers are then formed into a web or sheet, dried, and, optionally, sprayed with a solution of citric acid at a loading of about 2.5 weight percent of the fibers. The web is then packaged and shipped to end users for further processing, including fiberization to form individualized fibers useful in the manufacture of various products.

In another preferred embodiment, the treated fibers of the present invention are made from cellulose fiber obtained from GP Cellulose. The pulp is slurried, the pH is adjusted to about 4.0, and aluminum sulfate ($Al_2(SO_4)_3$) in aqueous solution is added to the slurry. The slurry is stirred and the consistency reduced. Under agitation, the pH of the slurry is increased to approximately 5.7. The fibers are then formed into a web or sheet, dried, and sprayed with a solution of sodium oleate at a loading of about 1.0 weight percent of the fibers. The web is then packaged and shipped to end users for further processing, including re-slurrying to form a web useful in the manufacture of filtration products. If a reducing agent is to be applied, preferably it is applied before a drying step and following any other application steps. The reducing agent may be applied by spraying, painting or foaming.

Metal ion content, including aluminum or iron content, in pulp samples can be determined by wet ashing (oxidizing) the sample with nitric and perchloric acids in a digestion apparatus. A blank is oxidized and carried through the same steps as the sample. The sample is then analyzed using an inductively coupled plasma spectrophotometer, such as, for example, a Perkin-Elmer ICP 6500. From the analysis, the ion content in the sample can be determined in parts per million. The polyvalent cation content desirably is from about 0.1 weight percent to about 5.0 weight percent, based on the dry weight of the treated fibers, more desirably, from about 0.1 weight percent to about 3.0 weight percent, based on the dry weight of the treated fibers, preferably from about 0.1 weight percent to about 1.5 weight percent, based on the dry weight of the treated fibers, more preferably, from about 0.2 weight percent to about 0.9 weight percent, based on the dry weight of the treated fibers, and more preferably from about 0.3 weight percent to about 0.8 weight percent, based on the dry weight of the treated fibers.

Without intending to be bound by theory, it is believed that by this process, the soluble $Al_2(SO_4)_3$ introduced to the pulp slurry is converted to insoluble $Al(OH)_3$ as the pH is increased. The insoluble aluminum hydroxide precipitates onto the fiber. Thus, the resultant chemically treated cellulose fibers are coated with $Al(OH)_3$ or contain the insoluble metal within the fiber interior.

The sodium oleate sprayed onto the web containing the fibers dries on the fibers. When the $Al(OH)_3$-oleate treated fibers are formed into a filter based sheet, the aluminum and oleate ions create a hydrophobic environment in addition to increasing the wet strength of the structure. These results are exemplified in the procedures set forth below.

In another embodiment, hydrated aluminum sulfate and sodium oleate are sprayed on the fiber after the drying section of a paper machine. In another embodiment, hydrated aluminum sulfate and sodium oleate are precipitated onto the fiber in the wet end section of a paper machine. In another embodiment, hydrated aluminum sulfate and sodium hypophosphite are sprayed on the fiber prior to the pressing stage, and sodium oleate is sprayed after drying. In another embodiment, hydrated aluminum sulfate, sodium hypophosphite and sodium oleate are sprayed on the fiber prior to the pressing stage. In yet another embodiment, hydrated aluminum sulfate is precipitated onto the fiber, hydrated aluminum and sodium hypophosphite are sprayed on the fiber prior to pressing, and sodium oleate is sprayed on the fiber after drying. In another embodiment, hydrated aluminum sulfate is precipitated onto the fiber and sodium oleate is sprayed on the fiber prior to the pressing stage.

Various materials, structures and manufacturing processes can be used in connection with the presently disclosed modified cellulose fibers, for example and not limitation, as described in U.S. Pat. Nos. 6,241,713, 6,353,148, 6,353,148, 6,171,441, 6,159,335, 5,695,486, 6,344,109, 5,068,079, 5,492,759, 5,269,049, 5,601,921, 5,693,162, 5,922,163, 6,007,653, 6,355,079, 6,403,857, 6,479,415, 6,562,742, 6,562,743, 6,559,081, 6,495,734, 6,420,626, and 8,946,100, and in U.S. Patent Publication Nos. US2004/0208175 and US2002/0013560, all of which are hereby incorporated by reference in their entireties.

In certain embodiments, chemically modified cellulose such as cross-linked cellulose fibers and highly purified cellulose fibers can be used. In particular embodiments, the modified cellulose fibers are crosslinked cellulose fibers. In certain embodiments, the modified cellulose fibers comprise a polyhydroxy compound. Non-limiting examples of polyhydroxy compounds include glycerol, trimethylolpropane, pentaerythritol, polyvinyl alcohol, partially hydrolyzed polyvinyl acetate, and fully hydrolyzed polyvinyl acetate.

In certain embodiments, the modified cellulose pulp fibers have been softened or plasticized to be inherently more compressible than unmodified pulp fibers. The same pressure applied to a plasticized pulp web will result in higher density than when applied to an unmodified pulp web. Additionally, the densified web of plasticized cellulose fibers is inherently softer than a similar density web of unmodified fiber of the same wood type. Softwood pulps may be made more compressible using cationic surfactants as debonders to disrupt interfiber associations. Use of one or more debonders facilitates the disintegration of the pulp sheet into fluff in the airlaid process. Examples of debonders include, but are not limited to, those disclosed in U.S. Pat. Nos. 4,432,833, 4,425,186 and 5,776,308, all of which are hereby incorporated by reference in their entireties. One example of a debonder-treated cellulose pulp is FFLE+. Plasticizers for cellulose, which can be added to a pulp slurry prior to forming wetlaid sheets, can also be used to soften pulp, although they act by a different mechanism than debonding agents. Plasticizing agents act within the fiber, at the cellulose molecule, to make flexible or soften amorphous regions. The resulting fibers are characterized as limp. Since the plasticized fibers lack stiffness, the comminuted pulp is easier to densify compared to fibers not treated with plasticizers. Plasticizers include, but are not limited to, polyhydric alcohols such as glycerol, low molecular weight polyglycol such as polyethylene glycols, and polyhydroxy compounds. These and other plasticizers are described and exemplified in U.S. Pat. Nos. 4,098,996, 5,547,541 and 4,731,269, all of which are hereby incorporated by reference in their entireties. Ammonia, urea, and alkylamines are also known to plasticize wood products, which mainly contain cellulose (A. J. Stamm, Forest Products Journal 5(6):413, 1955, hereby incorporated by reference in its entirety).

Binders

Suitable binders include, but are not limited to, liquid binders and powder binders. Non-limiting examples of liquid binders include emulsions, solutions, or suspensions of binders. Non-limiting examples of binders include polyethylene powders, copolymer binders, vinylacetate ethylene binders, styrene-butadiene binders, urethanes, urethane-based binders, acrylic binders, thermoplastic binders, natural polymer based binders, and mixtures thereof.

Suitable binders include, but are not limited to, copolymers, including vinyl-chloride containing copolymers such as Wacker VINNOL 4500, VINNOL 4514, and VINNOL 4530, vinylacetate ethylene ("VAE") copolymers, which can have a stabilizer such as Wacker VINNAPAS 192, Wacker VINNAPAS EF 539, Wacker VINNAPAS EP907, Wacker VINNAPAS EP129, Celanese DUROSET E130, Celanese Dur-O-Set Elite 130 25-1813 and Celanese Dur-O-Set TX-849, Celanese 75-524A, polyvinyl alcohol-polyvinyl acetate blends such as Wacker VINAC 911, vinyl acetate homopolymers, polyvinyl amines such as BASF Luredur, acrylics, cationic acrylamides, polyacryliamides such as Bercon BERSTRENGTH 5040 and Bercon BERSTRENGTH 5150, hydroxyethyl cellulose, starch such as National Starch CATO® 232, National Starch CATO® 255, National Starch Optibond, National Starch Optipro, or National Starch OptiPLUS, guar gum, styrene-butadienes, urethanes, urethane-based binders, thermoplastic binders, acrylic binders, and carboxymethyl cellulose such as Hercules Aqualon CMC. In certain embodiments, the binder is a natural polymer based binder. Non-limiting examples of natural polymer based binders include polymers derived from starch, cellulose, chitin, and other polysaccharides.

In certain embodiments, the binder is water-soluble. In one embodiment, the binder is a vinylacetate ethylene copolymer. One non-limiting example of such copolymers is EP907 (Wacker Chemicals, Munich, Germany). VINNAPAS EP907 can be applied at a level of about 10% solids incorporating about 0.75% by weight Aerosol OT (Cytec Industries, West Paterson, N.J.), which is an anionic surfactant. Other classes of liquid binders such as styrene-butadiene and acrylic binders can also be used.

In certain embodiments, the binder is not water-soluble. Examples of these binders include, but are not limited to, VINNAPAS 124 and 192 (Wacker), which can have an opacifier and whitener, including, but not limited to, titanium dioxide, dispersed in the emulsion. Other binders include, but are not limited to, Celanese Emulsions (Bridgewater, N.J.) Elite 22 and Elite 33.

In certain embodiments, the binder is a thermoplastic binder. Such thermoplastic binders include, but are not limited to, any thermoplastic polymer which can be melted at temperatures which will not extensively damage the cellulose fibers. Preferably, the melting point of the thermoplastic binding material will be less than about 175° C. Examples of suitable thermoplastic materials include, but are not limited to, suspensions of thermoplastic binders and thermoplastic powders. In particular embodiments, the thermoplastic binding material can be, for example, polyethylene, polypropylene, polyvinylchloride, and/or polyvinylidene chloride.

The binder can be non-crosslinkable or crosslinkable. In certain embodiments, the binder is WD4047 urethane-based binder solution supplied by HB Fuller. In one embodiment, the binder is Michem Prime 4983-45N dispersion of ethylene acrylic acid ("EAA") copolymer supplied by Michelman. In certain embodiments, the binder is Dur-O-Set Elite 22LV emulsion of VAE binder supplied by Celanese Emulsions (Bridgewater, N.J.). As noted above, in particular embodiments, the binder is crosslinkable. It is also understood that crosslinkable binders are also known as permanent wet strength binders. A permanent wet-strength binder includes, but is not limited to, Kymene® (Hercules Inc., Wilmington, Del.), Parez® (American Cyanamid Company, Wayne, N.J.), Wacker VINNAPAS or AF192 (Wacker Chemie AG, Munich, Germany), or the like. Various permanent wet-strength agents are described in U.S. Pat. Nos. 2,345,543, 2,926,116, and 2,926,154, the disclosures of which are incorporated by reference in their entirety. Other permanent wet-strength binders include, but are not limited to, polyamine-epichlorohydrin, polyamide epichlorohydrin or polyamide-amine epichlorohydrin resins, which are collectively termed "PAE resins". Non-limiting exemplary permanent wet-strength binders include Kymene 557H or Kymene 557LX (Hercules Inc., Wilmington, Del.) and have been described in U.S. Pat. Nos. 3,700,623 and 3,772,076, which are incorporated herein in their entirety by reference thereto.

Alternatively, in certain embodiments, the binder is a temporary wet-strength binder. The temporary wet-strength binders include, but are not limited to, Hercobond® (Hercules Inc., Wilmington, Del.), Parez® 750 (American Cyanamid Company, Wayne, N.J.), Parez® 745 (American Cyanamid Company, Wayne, N.J.), or the like. Other suitable temporary wet-strength binders include, but are not limited to, dialdehyde starch, polyethylene imine, mannogalactan gum, glyoxal, and dialdehyde mannogalactan. Other suitable temporary wet-strength agents are described in U.S. Pat. Nos. 3,556,932, 5,466,337, 3,556,933, 4,605,702, 4,603,176, 5,935,383, and 6,017,417, all of which are incorporated herein in their entirety by reference thereto.

In certain embodiments, binders are applied as emulsions in amounts ranging from about from about 1 gsm to about 15 gsm, or from about 2 gsm to about 10 gsm, or from about 2 gsm to about 8 gsm, or from about 3 gsm to about 5 gsm. The emulsion can further include one or more additional components. For example and not limitation, the emulsion can include one or more surfactants in an amount of from about 0.5 wt-% to about 1.5 wt-% based on the total weight of the emulsion. The binder, whether or not part of an emulsion, can be applied to one side of a fibrous layer, preferably an externally facing layer. Alternatively, binder can be applied to both sides of a layer, in equal or disproportionate amounts.

Other Additives

The materials of the presently disclosed subject matter can also contain other additives. For example, the materials can contain superabsorbent polymer (SAP). The types of superabsorbent polymers which may be used in the disclosed subject matter include, but are not limited to, SAPs in their particulate form such as powder, irregular granules, spherical particles, staple fibers and other elongated particles. U.S. Pat. Nos. 5,147,343; 5,378,528; 5,795,439; 5,807,916; 5,849,211, and 6,403,857, which are hereby incorporated by reference in their entireties, describe various superabsorbent polymers and methods of making superabsorbent polymers. One example of a superabsorbent polymer forming system is crosslinked acrylic copolymers of metal salts of acrylic acid and acrylamide or other monomers such as 2-acrylamido-2-methylpropanesulfonic acid. Many conventional granular superabsorbent polymers are based on poly(acrylic acid) which has been crosslinked during polymerization with any of a number of multifunctional co-monomer crosslinking agents well-known in the art. Examples of multi-functional crosslinking agents are set forth in U.S. Pat. Nos. 2,929,154; 3,224,986; 3,332,909; 4,076,673, which are incorporated herein by reference in their entireties. For instance, crosslinked carboxylated polyelectrolytes can be used to form superabsorbent polymers. Other water-soluble polyelectrolyte polymers are known to be useful for the preparation of superabsorbents by crosslinking, these polymers include: carboxymethyl starch, carboxymethyl cellulose, chitosan salts, gelatine salts, etc. They are not, however, commonly used on a commercial scale to enhance absorbency of dispensable absorbent articles mainly due to their higher cost. Superabsorbent polymer granules useful in the practice of this subject matter are commercially available from a number of manufacturers, such as BASF, Dow Chemical (Midland, Mich.), STOCKHAUSEN (Greensboro, N.C.), Chemdal (Arlington Heights, Ill.), and EVONIK (Essen, Germany). Non-limiting examples of SAP include a surface crosslinked acrylic acid based powder such as STOCKHAUSEN 9350 or SX70, BASF HYSORB FEM 33N, or EVONIK Favor SXM 7900.

In certain embodiments, SAP can be used in a layer in amounts ranging from about 5 wt-% to about 100 wt-% based on the total weight of the structure. In particular embodiments, a layer comprising 100 wt-% SAP can be disposed between two adjacent layers containing fibers. In certain embodiments, the amount of SAP in a layer can range from about 10 gsm to about 60 gsm, or from about 20 gsm to about 50 gsm, or from about 30 gsm to about 40 gsm.

Nonwoven Material

The presently disclosed subject matter provides for a nonwoven material that incorporates high core bicomponent fibers. As embodied herein, the nonwoven material can include at least one layer, at least two layers, at least three layers, at least four layers, at least five layers, at least six layers, at least seven layers, or at least eight layers, wherein at least one layer contains high core bicomponent fibers. Additionally, each layer can comprise a specific fibrous content, and as such can include other synthetic fibers and/or cellulose fibers.

As embodied herein, the nonwoven material can be an airlaid material. For example and not limitation, the material can be a thermally bonded airlaid (TBAL) material comprising high core bicomponent fibers. For further example, the material can be a multi-bonded airlaid (MBAL) material comprising high core bicomponent fibers and a binder.

In certain embodiments, the nonwoven material can include a single layer comprising high core bicomponent fibers. The layer can further include additional fiber types, such as other synthetic fibers and/or cellulose fibers. In certain embodiments, the single layer can further include low core bicomponent fibers. For example and not limitation, the high core bicomponent fibers can have a core to sheath ratio of about 7:3 and the low core bicomponent fibers can have a core to sheath ratio of about 3:7.

For further example, in particular embodiments, the nonwoven material can include at least two layers, wherein at least one layer contains high core bicomponent fibers. For example and not limitation, a first layer can contain high core bicomponent fibers and a second layer, adjacent to the first layer, can contain low core bicomponent fibers (i.e., bicomponent fibers having less than 50% core by weight). In certain embodiments, at least one of the first layer and the second layer can contain a blend of high core bicomponent fibers and low core bicomponent fibers. Thus, in certain embodiments, both layers of a two-layer structure can contain high core fibers and at least one of the layers can additionally include low core bicomponent fibers. Additionally, the first layer and the second layer can further include additional synthetic and/or cellulose fibers. In particular embodiments, the high core bicomponent fibers can have a core to sheath ratio of about 7:3 and the low core bicomponent fibers can have a core to sheath ratio of about 3:7.

Additionally, in certain embodiments, the nonwoven material can include a third layer, adjacent to the second layer. The third layer can optionally include high core bicomponent fibers and/or other fiber types such as low core bicomponent fibers, other synthetic fibers, and/or cellulose fibers. In specific embodiments, the first and third layers can comprise high core bicomponent fibers and the second, intermediate layer can comprise low core bicomponent fibers. In other specific embodiments, the first and third layers can comprise low core bicomponent fibers and the second, intermediate layer can comprise high core bicomponent fibers. One or more of the first, second, and third layers can additionally include cellulose fibers. In other certain embodiments, at least one layer does not include cellulose fibers. In certain embodiments, the nonwoven material includes three or fewer layers.

In certain embodiments, the nonwoven material can be a four layer substrate. The outer layers can include synthetic fibers, such as low core bicomponent fibers, whereas at least one intermediate layer includes high core bicomponent fibers. In certain embodiments, at least one of the outer layers can further include high core bicomponent fibers. One or more of the layers can additionally include cellulose fibers. In certain embodiments, both intermediate layers can comprise high core bicomponent fibers. Additionally or alternatively, at least one of the intermediate layers can include a blend of high core bicomponent fibers and low core bicomponent fibers.

Alternatively, a two layer material can comprise high core bicomponent fibers in a first layer and a second type of synthetic fibers in a second layer. This second type of synthetic fibers need not be high core or low core bicomponent fibers, and can instead be monocomponent fibers or conventional bicomponent fibers, e.g., having a 1:1 core to sheath ratio. Such conventional bicomponent fibers can also have a core-sheath configuration and can be formed of any suitable material, as known in the art. When bicomponent fibers are present in the second layer, the bicomponent fibers of the second layer can be formed from the same or different material as the high core bicomponent fibers. For example, in certain embodiments, both the high core bicomponent fibers in the first layer and the bicomponent fibers of the second layer can comprise a PET core and a polyethylene sheath, just with differing core to sheath ratios. In other embodiments, the bicomponent fibers of the second layer can comprise a different polymeric core material, such as polypropylene. Additionally or alternatively, in certain embodiments, the high core bicomponent fibers of the first layer can be concentric whereas the bicomponent fibers of the second layer can be eccentric.

The first layer, comprising high core bicomponent fibers, can further include additional fiber types such as low core bicomponent fibers, other synthetic fibers, and/or cellulose fibers. For example, the first layer can include cellulose fibers along with the high core bicomponent fibers. For example and not limitation, the cellulose fibers can comprise cellulose fluff and/or eucalyptus pulp. In certain embodiments, the cellulose fibers of a layer can comprise only hardwood fibers, such as eucalyptus fibers. Alternatively, the cellulose fibers of a layer can comprise a mixture of hardwood and softwood fibers. Alternatively, the cellulose fibers of a layer can comprise only softwood fibers. Additionally or alternatively, the first layer can be coated on at least of a portion of its outer surface with a binder. It is not necessary that the binder chemically bond with a portion of the layer, although it is preferred that the binder remain associated in close proximity with the layer, by coating, adhering, precipitation, or any other mechanism such that it is not dislodged from the layer during normal handling of the layer. For convenience, the association between the layer and the binder discussed above can be referred to as the bond, and the compound can be said to be bonded to the layer. If present, the binder can be applied in amounts ranging from about 1 gsm to about 15 gsm, or from about 2 gsm to about 10 gsm, or from about 2 gsm to about 8 gsm, or from about 3 gsm to about 5 gsm.

Overall, the first layer can have a basis weight of from about 5 gsm to about 100 gsm, or from about 5 gsm to about 80 gsm, or from about 10 gsm to about 60 gsm, or from about 20 gsm to about 50 gsm, or from about 25 gsm to about 45 gsm, or from about 30 gsm to about 40 gsm. When the first layer includes a blend of high core bicomponent fibers and another type of fiber, the high core bicomponent fibers can be present in an amount of from about 5 wt-% to about 100 wt-%, or from about 5 wt-% to about 75 wt-%, or from about 10 wt-% to about 50 wt-%, or from about 15 wt-% to about 40 wt-%, or from about 20 wt-% to about 35 wt-%.

In these embodiments, the second layer, comprising a second type of synthetic fibers, can have a basis weight of from about 5 gsm to about 100 gsm, or from about 5 gsm to about 75 gsm, or from about 5 gsm to about 50 gsm, or from about 10 gsm to about 45 gsm, or from about 15 gsm to about 40 gsm, or from about 20 gsm to about 35 gsm.

The material can optionally include a third layer, disposed between the first layer comprising high core bicomponent fibers and the second layer comprising a second type of bicomponent fibers, which can include synthetic and/or cellulose fibers. For example, in certain embodiments, the third layer can also contain synthetic fibers, such as bicomponent fibers. The bicomponent fibers of the third layer can be the same as or different than the bicomponent fibers of the second layer. The third layer can have a basis weight of from about 5 gsm to about 100 gsm, or from about 5 gsm to about 75 gsm, or from about 5 gsm to about 50 gsm, or from about 5 gsm to about 25 gsm, or from about 7 gsm to about 20 gsm, or from about 10 gsm to about 15 gsm.

In certain embodiments, the fiber types in the first layer, the second layer, and (if present) the third layer can be selected to create a directional density gradient through the nonwoven material in order to establish a specific pore and channel network within the nonwoven material.

In certain embodiments, one or more layers can contain fine fibers, which can create high capillary tension within the layer. Thus, such fine fibers can substitute for SAP or other absorbent materials and can assist with the distribution of liquid within the layers. Examples of such fine fibers are provided in Table 1, above. If present, fine fibers can be used in a particular layer in an amount of from about 0 wt-% to about 100 wt-%, or from about 0 wt-% to about 50 wt-%, or from about 50 wt-% to about 100 wt-%, or from about 70 wt-% to about 90 wt-%, or from about 70 wt-% to about 85 wt-%.

In additional embodiments, the nonwoven material can include at least three layers, of which at least the intermediate layer contains high core bicomponent fibers. For example, the intermediate layer can contain only high core bicomponent fibers, or can further include one or more additional types of fibers, such as other synthetic fibers and/or cellulose fibers. In particular embodiments, the intermediate layer can contain cellulose fibers, such as cellulose fluff and/or eucalyptus pulp. In such embodiments, the intermediate layer can comprise from about 5 wt-% to about 100 wt-%, or from about 5 wt-% to about 75 wt-%, or from about 10 wt-% to about 50 wt-%, or from about 15 wt-% to about 40 wt-%, or from about 20 wt-% to about 35 wt-%, or from about 25 wt-% to about 30 wt-% high core bicomponent fibers and from about 0 wt-% to about 95 wt-%, or from about 25 wt-% to about 95 wt-%, or from about 50 wt-% to about 90 wt-%, or from about 60 wt-% to about 85 wt-%, or from about 65 wt-% to about 80 wt-%, or from about 70 wt-% to about 75 wt-% cellulose fibers. The intermediate layer can additionally include other fibers such as other types of synthetic fibers. The intermediate layer can have a basis weight of from about 5 gsm to about 200 gsm, or from about 10 gsm to about 200 gsm, or from about 30 gsm to about 200 gsm, or from about 50 gsm to about 150 gsm, or from about 60 gsm to about 130 gsm, or from about 70 gsm to about 120 gsm, or from about 75 gsm to about 110 gsm.

As embodied herein, the layers adjacent to the intermediate layer can comprise any suitable fiber type, including synthetic and/or cellulose fibers. For example, the first layer, adjacent to the intermediate layer, can comprise a second type of synthetic fibers that need not be high core or low core bicomponent fibers, and can instead be monocomponent fibers or conventional bicomponent fibers having a 1:1 core to sheath ratio and can be formed of any suitable material, as known in the art. For example, the second bicomponent fibers can be formed from the same or different material as the high core bicomponent fibers. For example, in certain embodiments, both the second bicomponent fibers in the first layer can comprise a PET core or a polypropylene core and a polyethylene sheath. Additionally or alternatively, in certain embodiments, the high core bicomponent fibers of the intermediate layer can be concentric whereas the bicomponent fibers of the first layer can be eccentric.

The second layer, which is also adjacent to the intermediate layer and on the opposite side from the first layer, can also include any suitable fiber type, including synthetic and/or cellulose fibers. In particular embodiments, the second layer can comprise cellulose fibers, for example cellulose fluff and/or eucalyptus pulp. In certain embodiments, the cellulose fibers can have a Kajaani weighted average length of shorter than about 3.0 mm and a coarseness of finer than about 15 mg/100 m. The second layer can optionally further include synthetic fibers. In certain embodiments, the second layer can include bicomponent fibers in addition to cellulose fibers. The bicomponent fibers of the second layer can be the same as or different from the bicomponent fibers of the first layer (if present), and need not be high core bicomponent fibers. In certain embodiments, the bicomponent fibers of the second layer can be low core bicomponent fibers.

Overall, the second layer can have a basis weight of from about 5 gsm to about 100 gsm, or from about 10 gsm to about 100 gsm, or from about 30 gsm to about 100 gsm, or from about 40 gsm to about 90 gsm, or from about 50 gsm to about 80 gsm, or from about 60 gsm to about 70 gsm. In certain embodiments, the second layer can be heavier than the first layer and/or the third layer (if present). In alternative embodiments, the first layer can be heavier than the second layer. When the first layer includes a blend of bicomponent fibers and cellulose fibers, the bicomponent fibers can be present in an amount of from about 5 wt-% to about 100 wt-%, or from about 5 wt-% to about 75 wt-%, or from about 5 wt-% to about 50 wt-%, or from about 5 wt-% to about 25 wt-%, or from about 10 wt-% to about 15 wt-% and the cellulose fibers can be present in an amount of from about 0 wt-% to about 95 wt-%, or from about 25 wt-% to about 95 wt-%, or from about 50 wt-% to about 95 wt-%, or from about 75 wt-% to about 95 wt-%, or of from about 85 wt-% to about 90 wt-%.

In certain embodiments, at least one of the first layer and the second layer can be coated on at least of a portion of its outer surface with a binder. If present, the binder can be applied in amounts ranging from about 1 gsm to about 30 gsm, or from about 1 gsm to about 20 gsm, or from about 1 gsm to about 15 gsm, or from about 2 gsm to about 10 gsm, or from about 2 gsm to about 8 gsm, or from about 3 gsm to about 5 gsm. The binder can optionally be applied as an emulsion further containing a surfactant.

Additionally, in certain embodiments, the nonwoven material can further include a layer of SAP. This layer can be an intermediate layer that is disposed between a layer containing high core bicomponent fibers and another layer. The layer of SAP can comprise from about 10 gsm to about 100 gsm, or from about 10 gsm to about 80 gsm, or from about 10 gsm to about 70 gsm, or from about 20 gsm to about 60 gsm, or from about 30 gsm to about 50 gsm of SAP, or from about 40 gsm to about 50 gsm.

In embodiments having both cellulose and bicomponent fibers, the overall material can contain from about 5 wt-% to about 100 wt-%, or from about 5 wt-% to about 75 wt-%, or from about 10 wt-% to about 50 wt-%, or from about 15 wt-% to about 50 wt-%, or from about 20 wt-% to about 40 wt-%, or from about 25 wt-% to about 35 wt-% bicomponent fibers and from about 0 wt-% to about 95 wt-%, or from about 25 wt-% to about 95 wt-%, or from about 50 wt-% to about 90 wt-%, or from about 50 wt-% to about 85 wt-%, or from about 60 wt-% to about 80 wt-%, or from about 65 wt-% to about 75 wt-% cellulose fibers.

In certain embodiments, the range of basis weight of the nonwoven material is from about 50 gsm to about 500 gsm, or from about 50 gsm to about 400 gsm, or from about 50 gsm to about 300 gsm, or from about 50 gsm to about 250 gsm, or from about 100 gsm to about 500 gsm, or from about 200 gsm to about 400 gsm, or from about 200 gsm to about 300 gsm. The caliper of the nonwoven material, inclusive of all layers, can be from about 0.1 mm to about 8.0 mm, or from about 0.1 mm to about 7.5 mm, or from about 0.5 mm to about 6.0 mm, or from about 0.5 mm to about 4.0 mm, or from about 1.0 mm to about 4.0 mm, or from about 1.0 mm to about 3.5 mm.

Methods of Making the Nonwoven Material

A variety of processes can be used to assemble the materials used in the practice of this disclosed subject matter to produce the materials, including but not limited to, traditional dry forming processes such as airlaying and carding or other forming technologies such as spunlace or airlace. Preferably, the materials can be prepared by airlaid processes. Airlaid processes include, but are not limited to, the use of one or more forming heads to deposit raw materials of differing compositions in selected order in the manufacturing process to produce a product with distinct strata. This allows great versatility in the variety of products which can be produced.

In one embodiment, the material is prepared as a continuous airlaid web. The airlaid web is typically prepared by disintegrating or defiberizing a cellulose pulp sheet or sheets, typically by hammermill, to provide individualized fibers. Rather than a pulp sheet of virgin fiber, the hammermills or other disintegrators can be fed with recycled airlaid edge trimmings and off-specification transitional material produced during grade changes and other airlaid production waste. Being able to thereby recycle production waste would contribute to improved economics for the overall process. The individualized fibers from whichever source, virgin or recycled, are then air conveyed to forming heads on the airlaid web-forming machine. A number of manufacturers make airlaid web forming machines suitable for use in the disclosed subject matter, including Dan-Web Forming of Aarhus, Denmark, M&J Fibretech A/S of Horsens, Denmark, Rando Machine Corporation, Macedon, N.Y. which is described in U.S. Pat. No. 3,972,092, Margasa Textile Machinery of Cerdanyola del Valles, Spain, and DOA International of Wels, Austria. While these many forming machines differ in how the fiber is opened and air-conveyed to the forming wire, they all are capable of producing the webs of the presently disclosed subject matter. The Dan-Web forming heads include rotating or agitated perforated drums, which serve to maintain fiber separation until the fibers are pulled by vacuum onto a foraminous forming conveyor or forming wire. In the M&J machine, the forming head is basically a rotary agitator above a screen. The rotary agitator may comprise a series or cluster of rotating propellers or fan blades. Other fibers, such as a synthetic thermoplastic fiber, are opened, weighed, and mixed in a fiber dosing system such as a textile feeder supplied by Laroche S. A. of Cours-La Ville, France. From the textile feeder, the fibers are air conveyed to the forming heads of the airlaid machine where they are further mixed with the comminuted cellulose pulp fibers from the hammer mills and deposited on the continuously moving forming wire. Where defined layers are desired, separate forming heads may be used for each type of fiber. Alternatively or additionally, one or more layers can be prefabricated prior to being combined with additional layers, if any. In certain embodiments, the forming wire can be patterned, such that at least one layer of the resulting nonwoven material is patterned.

The airlaid web is transferred from the forming wire to a calendar or other densification stage to densify the web, if necessary, to increase its strength and control web thickness. In one embodiment, the fibers of the web are then bonded by passage through an oven set to a temperature high enough to fuse the included thermoplastic or other binder materials. In a further embodiment, secondary binding from the drying or curing of a latex spray or foam application occurs in the same oven. The oven can be a conventional through-air oven, be operated as a convection oven, or may achieve the necessary heating by infrared or even microwave irradiation. In particular embodiments, the airlaid web can be treated with additional additives before or after heat curing. The airlaid web can optionally be embossed or otherwise patterned. Subsequently, the airlaid web can be rolled into bale on a roller.

Applications and Features of the Nonwoven Material

The nonwoven materials of the disclosed subject matter can be used for any application as known in the art. The nonwoven materials can be used alone or as a component in other consumer products. For example, the nonwoven materials can be used either alone or as a component in a variety of absorbent articles, including cleaning articles, personal care wipes, baby diapers, adult incontinence products, sanitary napkins and the like. Absorbent cleaning products include wipes, sheets, towels, and the like. The absorbency of the nonwoven materials can aid in dirt and mess removal in such cleaning applications.

The use of high core bicomponent fibers can improve the resiliency of the resulting nonwoven material. Without being bound to a particular theory, it is believed that the resiliency is imparted by the core of the bicomponent fibers, which remains intact even when the sheath has melted to facilitate fiber to fiber bonding. At the same time, the bonding from the melted sheath can provide tensile strength to the nonwoven material. The improved resiliency can be obtained in both unembossed and embossed nonwoven materials, and the high core bicomponent fibers can also improve resistance to compaction during the nonwoven embossing process.

In certain aspects, the present disclosure relates to nonwoven materials having improved performance as a wet wipe, e.g., when treated with lotion. The presence of liquid in the nonwoven material can cause pulp fibers to absorb liquid and the wetting of the pulp fibers, typically from about 65 wt-% to about 85 wt-% of the nonwoven material, can saturate the fibers and lower the resistance of the wet nonwoven material to tension and compression. The use of high core bicomponent fibers in the nonwoven materials can protect the structures against wet collapse when subjected to this tension and/or compression, e.g., forces that are typically encountered during the converting of wet wipes.

In certain other aspects, the present disclosure relates to nonwoven materials with improved liquid acquisition and retention. Such materials can be used as an absorbent hygiene product component in baby diapers, adult incontinence products, sanitary napkins and the like. For example, International Patent Publication No. WO2016/115181A1, the contents of which are hereby incorporated by reference in their entirety, describes multi-layer nonwoven acquisition materials having high liquid acquisition speed and low rewet. The nonwoven materials of the present disclosure have new compositions and structures that are suitable for use in acquisition materials having improved absorbency performance. In such embodiments, the nonwoven material can be used in combination with an adsorbent core in an absorbent product.

Additionally, in certain aspects, the present disclosure provides a multi-layer nonwoven material having a 3D cross-sectional profile, which can create a pattern of indentations in the form of channels, dimples, holes, dashed lines, etc. Thus, the 3D structural profile can be perpendicular to the surface of the nonwoven material and can facilitate the transfer of the liquid through the nonwoven material, e.g., to an absorbent core. Additionally, absorbent structures having particular 3D profiles are described in U.S. Pat. No. 6,562,742, the contents of which are hereby incorporated by reference in their entirety. For example, liquid can travel more easily through the indentations, in which the caliper and basis weight of the nonwoven material are lower than the average caliper and basis weight of the nonwoven material. Preferably, these indentations are located on the surface of the liquid intake nonwoven which is closer to the surface of the core component of the absorbent system.

In certain other aspects, the present disclosure relates to unitary, multifunctional nonwoven materials that have liquid acquisition, retention, and storage functions and that can be used in baby diapers, adult incontinence products, sanitary napkins and the like. These materials can have improved liquid intake speed, improved rewet, high liquid retention, and high liquid distribution performance. For example, in such structures a layer comprising cellulose fibers can be disposed furthest from the body of the wearer, causing the material to have high liquid distribution performance and retaining a high amount of liquid before any leakage occurs, whether or not the nonwoven material contains SAP. The opposite layer, closest to the body of the wearer, can contain synthetic fibers.

The presently disclosed nonwoven materials can have improved mechanical properties. For example, the nonwoven materials can be incorporated into a wipe, e.g., a wipe that is wetted with a lotion. The nonwoven materials can have a cross-direction wet tensile strength of greater than about 100 gli, or greater than about 250 gli, or greater than about 300 gli, or greater than about 400 gli, or greater than about 430 gli, or greater than about 500 gli, or from about 100 gli to about 1500 gli, or from about 200 gli to about 1000 gli, or from about 300 gli to about 800 gli, or from about 400 gli to about 600 gli, or from about 430 gli to about 550 gli. The nonwoven materials can have a machine-direction wet tensile strength of greater than about 100 gli, or greater than about 200 gli, or greater than about 240 gli, or greater than about 300 gli, or greater than about 350 gli, or from about 100 gli to about 1500 gli, or from about 100 gli to about 1000 gli, or from about 200 gli to about 500 gli, or from about 240 gli to about 450 gli. The nonwoven materials can have a machine-direction dry tensile strength of greater than about 100 gli, or greater than about 200 gli, or greater than about 300 gli, or greater than about 400 gli, or greater than about 500 gli, or greater than about 600 gli, or greater than about 650 gli, or greater than about 690 gli, or greater than about 750 gli, or greater than about 800 gli, or greater than about 840 gli, or from about 100 gli to about 1500 gli, or from about 300 gli to about 1000 gli, or from about 650 gli to about 900 gli, or from about 690 gli to about 870 gli. Additionally, the nonwoven materials can have a cross-direction wet elongation at peak load of greater than about 10%, or greater than about 15%, or greater than about 17%, or greater than about 20%, or from about 10% to about 30%, or from about 15% to about 30%, or from about 15% to about 25%. The nonwoven materials can have a machine-direction dry elongation at peak load of greater than about 5%, or greater than about 8%, or greater than about 10%, or greater than about 12%, or from about 5% to about 20%, or from about 8% to about 20%, or from about 10% to about 15%.

Additionally, the presently disclosed nonwoven materials can have improved fluid acquisition characteristics. A person having ordinary skill in the art will appreciate that the absorbency characteristics of a nonwoven material can vary. For example, the observed absorbency characteristics can vary based on the amount of fluid and the surface area of the nonwoven material. Additionally, when the nonwoven materials contain an absorbent core (either as a separate component or within a unitary, multifunctional structure), the materials can have improved fluid acquisition characteristics and can quickly absorb a fluid. In certain embodiments, a nonwoven material as described above can absorb a fluid in less than about 60 seconds, less than about 45 seconds, or less than about 30 seconds even with repeated (e.g., 2, 3, or more) insults. The time it takes for a material to absorb a fluid can be called an "acquisition time." For example, and not limitation, the acquisition time can be measured using the procedures described in Example 4, below.

Furthermore, the presently disclosed nonwoven materials can have improved dryness characteristics, indicating improved fluid retention. For example, after absorbing a fluid, the nonwoven materials can be pressed to measure the amount of fluid released. In certain embodiments, a rewet test can be used to press the nonwoven material and measure the released fluid, as described in Example 4, below. In certain embodiments, less than about 1 g, less than about 0.5 g, or less than about 0.1 g of fluid is released.

EXAMPLES

The following examples are merely illustrative of the presently disclosed subject matter and they should not be considered as limiting the scope of the subject matter in any way.

Example 1: Wet Wipe with Improved Resiliency and Folded Stack Height

The present Example provides for a multi-layer nonwoven substrate that can be used in a wet wipe and have improved resiliency under tension and compression and improved folded stack height in final form.

In this Example, a multi-layer nonwoven TBAL substrate was formed using a full-scale former. The substrate contained high core bicomponent fibers having a core to sheath ratio of 7:3 and a dtex of 1.7, as well as additional bicomponent fibers having a core to sheath ratio of 3:7. The substrate further contained GP 4725 cellulose pulp. The composition of the substrate is shown in Table 2, below. The substrate was formed as a sheet and wound into a roll at a winder tension of 90 to 95 N/m with a target roll density of 110 kg/m$^3$. The target caliper of the sheet prior to winding was 1.15 mm or higher, and the sheet was embossed prior to winding. The target basis weight for the sheet was 50 gsm.

TABLE 2

| | Composition |
|---|---|
| Layer 1 | 16.4 gsm GP 4725 |
| | 7.8 gsm PE/PET bicomponent fibers |
| | (3:7 core:sheath, 6 mm, 1.5 dtex) |
| Layer 2 | 9.6 gsm GP 4725 |
| | 3.9 gsm PE/PET bicomponent fibers |
| | (7:3 core:sheath, 6 mm, 1.7 dtex) |
| Layer 3 | 4.1 gsm GP 4725 |
| | 1.9 gsm PE/PET bicomponent fibers |
| | (3:7 core:sheath, 6 mm, 1.5 dtex) |
| Layer 4 | 4.1 gsm GP 4725 |
| | 1.9 gsm PE/PET bicomponent fibers |
| | (3:7 core:sheath, 6 mm, 1.5 dtex) |

Prior to winding the sheets, several measurements were taking of the caliper, basis weight, and tensile strength of the substrates across six samples. Table 3, below, presents the average initial caliper, basis weight, cross-direction wet tensile strength, cross-direction wet elongation, machine-direction dry tensile strength, and machine-direction dry elongation for the six samples, along with the average caliper after winding for the six samples.

TABLE 3

|  | Average (6 samples) |
|---|---|
| Caliper (initial) | 1.18 mm |
| Basis Weight | 51.99 gsm |
| CD Wet Tensile | 438.78 gli |
| CD Wet Elongation | 17.54% |
| MD Dry Tensile | 695.54 gli |
| MD Dry Elongation | 10.97% |
| Caliper (after winding) | 0.99 mm |

Subsequently, 21 additional samples were prepared and tested, using the same composition and procedures. Similarly, the average initial caliper, basis weight, cross-direction wet tensile strength, cross-direction wet elongation, machine-direction dry tensile strength, and machine-direction dry elongation for the 21 samples prior to winding, along with the average caliper after winding were measured and are presented in Table 4, below.

TABLE 4

|  | Average (21 samples) |
|---|---|
| Caliper (initial) | 1.15 mm |
| Basis Weight | 52.15 gsm |
| CD Wet Tensile | 516.17 gli |
| CD Wet Elongation | 21.73% |
| MD Dry Tensile | 842.83 gli |
| MD Dry Elongation | 13.18% |
| Caliper (after winding) | 1.01 mm |

Taking the samples from Tables 2 and 3 together, the overall average caliper was 1.16 mm at the reel (i.e., prior to winding) and 1.01 mm after winding. The average roll density was approximately 113 kg/m³ prior to winding and 122 kg/m³ after winding.

Example 2: Pilot Scale Testing of Wet Wipes Having Improved Resiliency

This Example compares the caliper of wet wipes including high core bicomponent fibers with that of wet wipes having other bicomponent fibers.

Airlaid nonwoven samples were prepared, each having a total basis weight of 49.5 gsm with 3 layers of different fiber mixtures. Each sample included 30 wt-% bicomponent fibers and 70 wt-% cellulose fibers. The bicomponent fibers had a polyethylene sheath and a poly(ethylene terephthalate) (PET) core, with a dtex of 1.5 and 1.7 dtex and a length of 6 mm. The bicomponent fibers had a core to sheath ratio of either 3:7 or 7:3. The cellulose fibers were GP 4725 pulp. All samples were heat-cured at 138° C.

The compositions of Samples 2A-2C are provided in Table 5. Sample 2A was constructed with outer layers containing 75% of bicomponent fibers having a core to sheath ratio of 3:7 and 25% high core bicomponent fibers. A middle layer contained 100% bicomponent fibers having a core to sheath ratio of 3:7. Sample 2B was constructed with outer layers containing 50% of bicomponent fibers having a core to sheath ratio of 3:7 and 50% of high core bicomponent fibers. A middle layer contained 100% bicomponent fibers having a core to sheath ratio of 3:7. Sample 2C was constructed nearly identically to Sample 2A, with outer layers containing 75% of bicomponent fibers having a core to sheath ratio of 3:7 and 25% high core bicomponent fibers and a middle layer containing 100% bicomponent fibers having a core to sheath ratio of 3:7. However, in Sample 2C, the high core bicomponent fibers had a PE sheath polymer with a High Melt Flow ("HMF") to promote enhanced bonding of the sheath material.

TABLE 5

| Sample 2A | 1 | 2.1 gsm PE/PET bicomponent fibers (3:7 core:sheath, 6 mm, 1.5 dtex) |
|---|---|---|
|  |  | 6.3 gsm PE/PET bicomponent fibers (7:3 core:sheath, 6 mm, 1.7 dtex) |
|  |  | 16.6 gsm GP 4725 |
|  | 2 | 2.6 gsm PE/PET bicomponent fibers (3:7 core:sheath, 6 mm, 1.5 dtex) |
|  |  | 9.4 gsm GP 4725 |
|  | 3 | 1.0 gsm PE/PET bicomponent fibers (3:7 core:sheath, 6 mm, 1.5 dtex |
|  |  | 3.0 gsm PE/PET bicomponent fibers (7:3 core:sheath, 6 mm, 1.7 dtex) |
|  |  | 8.5 gsm GP 4725 |
| Sample 2B | 1 | 4.2 gsm PE/PET bicomponent fibers (3:7 core:sheath, 6 mm, 1.5 dtex) |
|  |  | 4.2 gsm PE/PET bicomponent fibers (7:3 core:sheath, 6 mm, 1.7 dtex) |
|  |  | 16.6 gsm GP 4725 |
|  | 2 | 2.6 gsm PE/PET bicomponent fibers (3:7 core:sheath, 6 mm, 1.5 dtex) |
|  |  | 9.4 gsm GP 4725 |
|  | 3 | 2.0 gsm PE/PET bicomponent fibers (3:7 core:sheath, 6 mm, 1.5 dtex |
|  |  | 2.0 gsm PE/PET bicomponent fibers (7:3 core:sheath, 6 mm, 1.7 dtex) |
|  |  | 8.5 gsm GP 4725 |
| Sample 2C | 1 | 2.1 gsm PE/PET bicomponent fibers (3:7 core:sheath, 6 mm, 1.5 dtex) |
|  |  | 6.3 gsm PE/PET bicomponent fibers, HMF (7:3 core:sheath, 6 mm, 1.7 dtex) |
|  |  | 16.6 gsm GP 4725 |
|  | 2 | 2.6 gsm PE/PET bicomponent fibers (3:7 core:sheath, 6 mm, 1.5 dtex) |
|  |  | 9.4 gsm GP 4725 |
|  | 3 | 1.0 gsm PE/PET bicomponent fibers (3:7 core:sheath, 6 mm, 1.5 dtex |
|  |  | 3.0 gsm PE/PET bicomponent fibers, HMF (7:3 core:sheath, 6 mm, 1.7 dtex) |
|  |  | 8.5 gsm GP 4725 |

The dry caliper of each sample was measured and are provided in Table 6. The increase in caliper of Sample 2A as compared to Sample 2B was 3.4%. In comparison, there was an increase of 6.7% between Sample 2C and Sample 2B. These improved calipers of Samples 2A and 2C are due to the increased content of bicomponent fibers having core to sheath ratios of 7:3, which thus have cores of larger cross-section, which impart increased caliper development versus the low core bicomponent fiber.

to sheath ratio of 1:1, with a polyethylene sheath, PET core, dtex of 2.2 dtex, and a length of 6 mm. The cellulose fibers were GP 4725 pulp.

TABLE 7

|  |  | Layer Composition | Basis Weight (Relative) |
|---|---|---|---|
| Control | 1 | PE/PET bicomponent fibers (3:7 core:sheath, 6 mm, 1.5 dtex) GP 4725 | 25 gsm (Heavy) |
|  | 2 | PE/PET bicomponent fibers (3:7 core:sheath, 6 mm, 1.5 dtex) GP 4725 | 11.8 gsm (Thin) |
|  | 3 | PE/PET bicomponent fibers (3:7 core:sheath, 6 mm, 1.5 dtex) GP 4725 | 12.5 gsm (Thin) |
| Sample 3A | 1 | PE/PP bicomponent fibers (7:3 core:sheath; 6 mm, 1.7 dtex) GP 4725 | 25 gsm (Heavy) |
|  | 2 | PE/PP bicomponent fibers (7:3 core:sheath; 6 mm, 1.7 dtex) GP 4725 | 11.8 gsm (Thin) |
|  | 3 | PE/PP bicomponent fibers (7:3 core:sheath; 6 mm, 1.7 dtex) GP 4725 | 12.5 gsm (Thin) |
| Sample 3B | 1 | PE/PET bicomponent fibers (1:1 core:sheath, 6 mm, 2.2 dtex) GP 4725 | 25 gsm (Heavy) |
|  | 2 | PE/PET bicomponent fibers (1:1 core:sheath, 6 mm, 2.2 dtex) GP 4725 | 11.8 gsm (Thin) |
|  | 3 | PE/PET bicomponent fibers (1:1 core:sheath, 6 mm, 2.2 dtex) GP 4725 | 12.5 gsm (Thin) |
| Sample 3C | 1 | PE/PET bicomponent fibers (3:7 core:sheath, 6 mm, 1.5 dtex) GP 4725 | 25 gsm (Heavy) |
|  | 2 | PE/PET bicomponent fibers (7:3 core:sheath, 6 mm, 1.7 dtex) GP 4725 | 11.8 gsm (Thin) |
|  | 3 | PE/PET bicomponent fibers (3:7 core:sheath, 6 mm, 1.5 dtex) GP 4725 | 12.5 gsm (Thin) |
| Sample 3D | 1 | PE/PET bicomponent fibers (3:7 core:sheath, 6 mm, 1.5 dtex) GP 4725 | 12.5 gsm (Thin) |
|  | 2 | PE/PET bicomponent fibers (7:3 core:sheath, 6 mm, 1.7 dtex) GP 4725 | 25 gsm (Heavy) |
|  | 3 | PE/PET bicomponent fibers (3:7 core:sheath, 6 mm, 1.5 dtex) GP 4725 | 12.5 gsm (Thin) |
| Sample 3E | 1 | PE/PET bicomponent fibers (7:3 core:sheath, 6 mm, 1.7 dtex) GP 4725 | 25 gsm (Heavy) |
|  | 2 | PE/PET bicomponent fibers (7:3 core:sheath, 6 mm, 1.7 dtex) GP 4725 | 11.8 gsm (Thin) |
|  | 3 | PE/PET bicomponent fibers (7:3 core:sheath, 6 mm, 1.7 dtex) GP 4725 | 12.5 gsm (Thin) |

TABLE 6

|  | Caliper (mm) | % Increase |
|---|---|---|
| Sample 2A | 1.54 | 3.4% |
| Sample 2B | 1.49 | — |
| Sample 2C | 1.59 | 6.7% |

Example 3: Stack Height of Wet Wipes Having High Core Bicomponent Fibers

This Example compares the stack height of wet wipes including high core bicomponent fibers with that of wet wipes having other bicomponent fibers.

Airlaid nonwoven samples were prepared, each having a total basis weight of 50 gsm with 3 layers of different fiber mixtures, according to Table 7, below. Each sample included 30 wt-% bicomponent fibers and 70 wt-% cellulose fibers. The high core bicomponent fibers had a polyethylene sheath and either a poly(ethylene terephthalate) (PET) or a polypropylene (PP) core, with a dtex of 1.7 dtex and a length of 6 mm and a core to sheath ratio of 7:3. The low core bicomponent fibers had a polyethylene sheath and PET core, with a dtex of 1.5 dtex and a length of 6 mm, and a core to sheath ratio of 3:7. Additional bicomponent fibers had a core The stack height of the 6 samples was measured and compared to the stack height of the control material having low core bicomponent fibers (i.e., having a core to sheath ratio of 3:7). The samples were cut into thirty (30) sheets measuring 6.8 in.×7.5 in. The sheets were folded and stacked. The pieces were sprayed with an aqueous personal wipe lotion with the add-on rate of the lotion being 3.05 times the weight of the wipes substrate. The substrates were then "C" folded together with the center overlap area of the wipes being 100-105 mm wide. The 30 folded and stacked wipes were then placed in a topless and bottomless Plexiglas box with inside dimensions of 112 mm×182 mm. A 1795 gram block (110 mm×180 mm×100 mm h outside dimensions) was placed on top of the wipes inside the box. After 1 hour, the height of the four corners of the stack of wipes was measured. Then, the block and box were removed from the wipes. After 30 minutes of rest, the four corner heights were then measured again. The corner measurements were averaged and compared against the control.

The stack heights of each sample and the control under pressure are presented in FIG. 1. This post-compression stack height of a wetted sample indicates the wet resilience of the sample, which is a critical parameter for wet wipes in converting, packaging, and customer preference. The samples containing a blend of high core bicomponent fibers with a core to sheath ratio of 7:3 were found to have higher stack heights, especially when combined with additional bicomponent fibers having a core to sheath ratio of 3:7 (e.g., Samples 3C and 3D). Thus, the addition of high core bicomponent fibers can improve the resiliency and recovery of nonwoven thickness. By comparison, the PE/PET bicomponent fibers having a core to sheath ratio of 1:1 did not improve the stack height of the material (see Sample 3B). This improvement is further illustrated in FIG. 2, which shows the percentage increase in stack height for each of the samples as compared to the control material. Samples 3C and 3D, which contained bicomponent fibers with two different core to sheath ratios—7:3 and 3:7—in different configurations had significantly improved stack height as compared to the control, and Samples 3A and 3E, which contained only high core bicomponent fibers (either with polypropylene or PET cores) having a core to sheath ratio of 7:3, also had improved stack high as compared to the control.

Additionally, the machine-direction wet tensile strength of each sample was measured and compared to that of the control, as shown in FIG. 3. In general, reducing the amount of polyethylene in the bicomponent fibers reduced the strength of the resulting material, and therefore, the samples containing the high core bicomponent fibers were found to 255, 1.5 dtex, 6 mm) mixed with 23.3 gsm of cellulose (GP-4723, fully-treated pulp from GP Cellulose), which was bonded with 3.8 gsm of polymeric binder in the form of an emulsion (VINNAPAS 192, Wacker) and 0.12 gsm of a surfactant (Aerosol OT 75, Cytec Industries).

Sample 4B was also formed using a pilot drum-forming machine, and had the same composition as Sample 4A in its top and middle layers. However, the bottom layer of Sample 4B was composed of 11.3 gsm of high core concentric bicomponent fibers having a PET core and a polyethylene sheath and a core to sheath ratio of 7:3 (TREVIRA, Type 255, 1.7 dtex, 6 mm) mixed with 23.3 gsm of cellulose (GP-4723, fully-treated pulp from GP Cellulose), which was bonded with a 3.8 gsm of polymeric binder in the form of an emulsion (VINNAPAS 192, Wacker) and 0.12 gsm of a surfactant (Aerosol OT 75, Cytec Industries).

Sample 4C was likewise formed using a pilot drum-forming machine. Sample 4C included a top layer having the same composition as those of Samples 4A and 4B. Sample 4C further included a bottom layer having the same composition as that of Sample 4B. The middle layer of Sample 4C was composed of 12.8 gsm of eccentric bicomponent fibers (FIBERVISIONS, 5.7 dtex, 6 mm, PE/PET).

Table 8, below, provides a pictorial description of the compositions of Samples 4A-4C:

TABLE 8

| | Layer | Composition |
|---|---|---|
| Sample 4A | Top | 24 gsm eccentric bico (PE/PET, 5.7 dtex, 6 mm) |
| | Middle | 12.8 gsm eccentric bico (PE/PP, 3.3 dtex, 4 mm) |
| | Bottom | 23.3 gsm cellulose fluff (GP-4723) |
| | | 11.3 gsm concentric bico (PE/PET, 1.5 dtex, 6 mm, 30% core) |
| | | 3.8 gsm Vinnapas 192 |
| Sample 4B | Top | 24 gsm eccentric bico (PE/PET, 5.7 dtex, 6 mm) |
| | Middle | 12.8 gsm eccentric bico (PE/PP, 3.3 dtex, 4 mm) |
| | Bottom | 23.3 gsm cellulose fluff (GP-4723) |
| | | 11.3 gsm concentric bico (PE/PET, 1.5 dtex, 6 mm, 70% core) |
| | | 3.8 gsm Vinnapas 192 |
| Sample 4C | Top | 24 gsm eccentric bico (PE/PET, 5.7 dtex, 6 mm) |
| | Middle | 12.8 gsm eccentric bico (PE/PET, 5.7 dtex, 6 mm) |
| | Bottom | 23.3 gsm cellulose fluff (GP-4723) |
| | | 11.3 gsm concentric bico (PE/PET, 1.5 dtex, 6 mm, 70% core) |
| | | 3.8 gsm Vinnapas 192 | have reduced tensile strength. Regardless, these materials, especially Samples 3C and 3D, were found to have sufficient tensile strength for incorporation into a nonwoven wipe material.

Example 4: Three-Layer Acquisition Material

In this Example, three samples each having three layers were prepared to test the effect of high core bicomponent fibers on liquid acquisition. Sample 4A was prepared without high core bicomponent fibers, whereas Samples 4B and 4C contained high core bicomponent fibers. Sample 4A was a two-sided nonwoven airlaid material and was formed using a pilot drum-forming machine. The top layer of Sample 4A was composed of 24 gsm of eccentric bicomponent fibers having a PET core and a polyethylene sheath (FIBERVISIONS, 5.7 dtex, 6 mm, PE/PET). The middle layer was composed of 12.8 gsm of eccentric bicomponent fibers having a polypropylene core and a polyethylene sheath (FIBERVISIONS, 3.3 dtex, 4 mm, PE/PP). The bottom layer was composed of 11.3 gsm of concentric bicomponent fibers having a PET core and a polyethylene sheath and a core to sheath ratio of 3:7 (TREVIRA, Type The liquid acquisition characteristics of each sample were evaluated in the following manner. A commercially available diaper was deconstructed. The original through-air bonded carded web (TABCW) from the deconstructed diaper was removed and replaced by one of Samples 4A, 4B, and 4C (basis weights=76.4 gsm, 75.0 gsm, and 74.2 gsm, respectively). Then the diaper's nonwoven topsheet was placed back on top of the sample. The diaper was then compressed with 4 bars of pressure via a roller press. The diaper was immediately tested by placing the diaper on top of a plastic encapsulated foam. A stainless-steel cylinder (with an inside diameter of 5 cm, an outside diameter of 7.2 cm, and weight of 324.8 g) was placed about 10 cm from the top of the diaper's frontside. 70 mL of 0.9% NaCl solution was poured into the cylinder. Acquisition Time #1 was measured from the moment the dosing of the liquid began until the liquid was no longer seen inside the stainless-steel cylinder. The stainless-steel cylinder was removed and metal plates (40.5 cm×10 cm, total weight of plates=10 kg) were placed on top of the diaper for 20 minutes. Acquisition Time #2 was then measured in the following manner. The metal plates (40.5 cm×10 cm, total weight of plates=10 kg) were removed. A stainless-steel cylinder (with an inside diameter of 5 cm, an outside diameter of 7.2 cm, and weight of 324.8 g) was placed about 10 cm from the top of the diaper's frontside. 70 mL of 0.9% NaCl solution was poured into the cylinder. Acquisition Time #2 was measured from the moment the dosing of the liquid began until the liquid was no longer seen inside the stainless-steel cylinder. The stainless-steel cylinder was removed and metal plates (40.5 cm×10 cm, total weight of plates=10 kg) were placed on top of the diaper for 20 minutes. Afterward, Acquisition Time #3 was measured in the same manner, whereby the metal plates (40.5 cm×10 cm, total weight of plates=10 kg) were removed. A stainless-steel cylinder (with an inside diameter of 5 cm, an outside diameter of 7.2 cm, and weight of 324.8 g) was placed about 10 cm from the top of the diaper's frontside. 70 mL of 0.9% NaCl solution was poured into the cylinder. Acquisition Time #3 was measured from the moment the dosing of the liquid began until the liquid was no longer seen inside the stainless-steel cylinder. The stainless-steel cylinder was removed and metal plates (40.5 cm×10 cm, total weight of plates=10 kg) were placed on top of the diaper for 20 minutes. A total of three acquisition times (#1, #2, and #3) were measured. The average acquisition times for each sample are provided in FIG. 4.

As shown in FIG. 4, the diaper with Sample 4A (which did not contain any high core bicomponent fibers) obstructed the flow of liquid into the diaper core more so than the diaper with Sample 4B. Because the difference between Samples 4A and 4B was the composition of the bottom layer, this result was achieved by the type of bicomponent fibers used in the bottom layer. Similarly, Sample 4C, which further included a difference in the middle layer, also had improved acquisition times as compared to Sample 4A. Not being bound by a particular theory, it is believed that the bicomponent fibers with higher polyester (PET) core content (e.g., Samples 4B and 4C) provide airlaid structures with more resiliency to collapse, which leads to preservation of the 3-dimensional stability of the fibrous network during mechanical compression of the diaper. This preservation of the bottom layer's 3-dimensional stability of the fibrous network can lead to faster fluid transport into the diaper's core, even with repeated liquid insults.

Example 5: Two-Layer Acquisition Material

In this Example, two samples each having two layers were prepared to test the effect of high core bicomponent fibers on liquid acquisition in textured and non-textured materials.

Sample 5A was a multi-functional, two-sided nonwoven airlaid material made using a lab padformer, in which the multi-functional attributes of acquisition, distribution, and storage are all integrated into one unitary structure. This nonwoven substrate consisted of a synthetic fiber acquisition layer, directionally layered to allow for acquisition and rewet, as well as a layer of eucalyptus pulp to provide storage.

The top layer of Sample 5A was composed of 33.7 gsm of eccentric bicomponent fibers having a PET core and a polyethylene sheath (FIBERVISIONS, ETE857G8, 5.7 dtex, 6 mm, PE/PET). The bottom layer was composed of 33.9 gsm of eucalyptus pulp (Suzann, untreated) mixed with 7.4 gsm of high core concentric bicomponent fibers having a PET core and a polyethylene sheath with a core to sheath ratio of 7:3 (TREVIRA, Type 255, 1.5 dtex, 6 mm). The composition of Sample 5A is shown in Table 9, below.

TABLE 9

|  | Layer | Composition |
|---|---|---|
| Sample 5A | Top | 33.7 gsm eccentric bico (PE/PET, 5.7 dtex, 6 mm) |
|  | Bottom | 33.9 gsm eucalyptus pulp (Suzano, untreated) |
|  |  | 7.4 gsm concentric bico (PE/PP, 1.5 dtex, 6 mm, 70% core) |

Sample 5B was also a multi-functional, two-sided nonwoven airlaid material made using a lab padformer and having the same structure and composition as Sample 5A (see Table 9). However, Sample 5B was produced on a patterned wire, which was inserted inside the lab padformer, resulting in a patterned bottom layer. FIG. 5A is a photograph of the 3D "textured" Sample 5B. FIG. 5B is an illustration of a 2D representation of the pattern of FIG. 5A.

The liquid acquisition characteristics of Samples 5A and 5B were evaluated in the following manner. A commercially available diaper was deconstructed. The original through-air bonded carded web (TABCW) from the deconstructed diaper was removed and replaced by one of Samples 5A and 5B (basis weights=75.0 gsm). Then the diaper's nonwoven topsheet was placed back on top of the sample. The diaper was then compressed with 4 bars of pressure via a roller press. The diaper was immediately tested by placing the diaper on top of a plastic encapsulated foam. A stainless-steel cylinder (with an inside diameter of 5 cm, an outside diameter of 7.2 cm, and weight of 324.8 g) was placed about 10 cm from the top of the diaper's frontside. 70 mL of 0.9% NaCl solution was poured into the cylinder. Acquisition Time #1 was measured from the moment the dosing of the liquid began until the liquid was no longer seen inside the stainless-steel cylinder. The stainless-steel cylinder was removed and metal plates (40.5 cm×10 cm, total weight of plates=10 kg) were placed on top of the diaper for 20 minutes. Acquisition Time #2 was then measured in the following manner. The metal plates (40.5 cm×10 cm, total weight of plates=10 kg) were removed. A stainless-steel cylinder (with an inside diameter of 5 cm, an outside diameter of 7.2 cm, and weight of 324.8 g) was placed about 10 cm from the top of the diaper's frontside. 70 mL of 0.9% NaCl solution was poured into the cylinder. Acquisition Time #2 was measured from the moment the dosing of the liquid began until the liquid was no longer seen inside the stainless-steel cylinder. The stainless-steel cylinder was removed and metal plates (40.5 cm×10 cm, total weight of plates=10 kg) were placed on top of the diaper for 20 minutes. Afterward, Acquisition Time #3 was measured in the same manner, whereby the metal plates (40.5 cm×10 cm, total weight of plates=10 kg) were removed. A stainless-steel cylinder (with an inside diameter of 5 cm, an outside diameter of 7.2 cm, and weight of 324.8 g) was placed about 10 cm from the top of the diaper's frontside. 70 mL of 0.9% NaCl solution was poured into the cylinder. Acquisition Time #3 was measured from the moment the dosing of the liquid began until the liquid was no longer seen inside the stainless-steel cylinder. The stainless-steel cylinder was removed and metal plates (40.5 cm×10 cm, total weight of plates=10 kg) were placed on top of the diaper for 20 minutes. A total of three acquisition times (#1, #2, and #3) were measured. The average acquisition times for each sample are provided in FIG. 6.

As shown in FIG. 6, the diaper with the 3D "textured" structure (Sample 5B) had improved Acquisition Time #3 (i.e., for the third insult) as compared to when this 3D profile structure was not included (Sample 5A), suggesting that the use of a textured layer can improve liquid acquisition with repeated insults of liquid.

Example 6: Multi-Layer Unitary Absorbent Nonwoven Material

In this Example, 8 sample multi-layer unitary structures (Samples 6A-6H) having integrated liquid acquisition, distribution. and storage functions and some of which contained super absorbent polymer (SAP) were compared to a control material to observe the effect of high core bicomponent fibers in varying amounts and placements. Each sample consisted of a synthetic fiber acquisition layer, directionally layered to allow for acquisition and rewet, as well as a multi-layer core structure to provide permanent storage with the use of SAP.

Sample 6A was a multi-layer unitary structure which was formed on a Danweb Airlaid Pilot Plant. 53 gsm of eucalyptus pulp (Suzann, untreated) was mixed with 7 gsm of bicomponent fibers having a PET core and a polyethylene sheath (TREVIRA Type 255-1663, 2.2 dtex, 3 mm) and deposited on the forming wire. Then, 35 gsm of Super Absorbent Polymer (SAP) (BASF Favor SXM 7900) was laid down on top of the first layer. The next layer consisted of 53 gsm of cellulose (Golden Isles® 4723, fully-treated pulp made by GP Cellulose) blended with 22 gsm of bicomponent fibers having a PET core and a polyethylene sheath (TREVIRA Type 255-1661, 2.2 dtex, 6 mm). The top layer was composed of 25 gsm eccentric bicomponent fibers having a polypropylene core and a polyethylene sheath (FIBERVISIONS PE/PP, 5.7 dtex, 4 mm). The bottom, eucalyptus layer was also sprayed with a 5 gsm polymeric binder in the form of an emulsion (VINNAPAS 192, Wacker+0.8% Aerosol OT75 surfactant). The total weight of the structure was calculated to be 200 gsm.

Sample 6B was a multi-layer unitary structure which was formed on a Danweb Airlaid Pilot Plant. 53 gsm of eucalyptus pulp (Suzann, untreated) was mixed with 7 gsm of bicomponent fibers having a PET core and a polyethylene sheath (TREVIRA Type 255-1663, 2.2 dtex, 3 mm) and deposited on the forming wire. Then, 35 gsm of Super Absorbent Polymer (SAP) (BASF Favor SXM 7900) was laid down on top of the first layer. The next layer consisted of 53 gsm of cellulose (Golden Isles® 4723, fully-treated pulp made by GP Cellulose) blended with 22 gsm of bicomponent fibers having a PET core with a polyethylene sheath and a core to sheath ratio of 7:3 (TREVIRA PE/PET 70% core, 1.7 dtex, 6 mm). The top layer was composed of 25 gsm of eccentric bicomponent fibers having a PET core and polyethylene sheath (FIBERVISIONS ETE857G8 PE/PET, 5.7 dtex, 6 mm). The bottom, eucalyptus layer was also sprayed with a 5 gsm polymeric binder in the form of an emulsion (VINNAPAS 192, Wacker+0.8% Aerosol OT75 surfactant). The total weight of the structure was calculated to be 200 gsm.

Sample 6C was a multi-layer unitary structure which was formed on a Danweb Airlaid Pilot Plant. 53 gsm of eucalyptus pulp (Suzann, untreated) was mixed with 7 gsm of bicomponent fibers having a PET core and a polyethylene sheath (TREVIRA Type 255-1663, 2.2 dtex 3 mm) and deposited on the forming wire. The next layer consisted of 80 gsm of cellulose (Golden Isles® 4723, fully-treated pulp made by GP Cellulose) blended with 30 gsm of bicomponent fibers having a PET core and a polyethylene sheath (TREVIRA Type 255-1661, 2.2 dtex, 6 mm). The top layer was composed of 25 gsm of eccentric bicomponent fibers having a polypropylene core and a polyethylene sheath (FIBERVISIONS PE/PP, 5.7 dtex, 4 mm). The bottom, eucalyptus layer was also sprayed with a 5 gsm polymeric binder in the form of an emulsion (VINNAPAS 192, Wacker+0.8% Aerosol OT75 surfactant). The total weight of the structure was calculated to be 200 gsm.

Sample 6D was a multi-layer unitary structure which was formed on a Danweb Airlaid Pilot Plant. 53 gsm of eucalyptus pulp (Suzann, untreated) was mixed with 7 gsm of bicomponent fibers having a PET core and a polyethylene sheath (TREVIRA Type 255-1663, 2.2 dtex, 3 mm) and deposited on the forming wire. The next layer consisted of 80 gsm of cellulose (Golden Isles® 4723, fully-treated pulp made by GP Cellulose) blended with 30 gsm of high core bicomponent fibers having a PET core and polyethylene sheath with a core to sheath ratio of 7:3 (TREVIRA PE/PET 70% core, 1.7 dtex, 6 mm). The top layer was composed of 25 gsm of eccentric bicomponent fibers (FIBERVISIONS PE/PP, 5.7 dtex, 4 mm). The bottom, eucalyptus layer was also sprayed with a 5 gsm polymeric binder in the form of an emulsion (VINNAPAS 192, Wacker+0.8% Aerosol OT75 surfactant). The total weight of the structure was calculated to be 200 gsm.

Sample 6E was a multi-layer unitary structure which was formed on a Danweb Airlaid Pilot Plant. 53 gsm of eucalyptus pulp (Suzann, untreated) was mixed with 7 gsm of bicomponent fibers having a PET core and a polyethylene sheath (TREVIRA Type 255-1663, 2.2 dtex, 3 mm) and deposited on the forming wire. The next layer consisted of 80 gsm of cellulose (Golden Isles® 4723, fully-treated pulp made by GP Cellulose) blended with 30 gsm of high core bicomponent fibers having a PET core and polyethylene sheath with a core to sheath ratio of 7:3 (TREVIRA PE/PET 70% core, 1.7 dtex, 6 mm). The top layer was composed of 25 gsm of eccentric bicomponent fibers having a PET core and a polyethylene sheath (FIBERVISIONS ETE857G8 PE/PET, 5.7 dtex, 6 mm). The bottom, eucalyptus layer was also sprayed with a 5 gsm polymeric binder in the form of an emulsion (VINNAPAS 192, Wacker+0.8% Aerosol OT75 surfactant). The total weight of the structure was calculated to be 200 gsm.

Sample 6F was a multi-layer unitary structure which was formed on a Danweb Airlaid Pilot Plant. 53 gsm of eucalyptus pulp (Suzann, untreated) was mixed with 7 gsm of bicomponent fibers having a PET core and a polyethylene sheath with a core to sheath ratio of 3:7 (TREVIRA PE/PET 30% core, 1.7 dtex, 6 mm) and deposited on the forming wire. The next layer consisted of 80 gsm of cellulose (Golden Isles® 4723, fully-treated pulp made by GP Cellulose) blended with 30 gsm of high core bicomponent fibers having a PET core and a polyethylene sheath with a core to sheath ratio of 7:3 (TREVIRA PE/PET 70% core, 1.7 dtex, 6 mm). The top layer was composed of 25 gsm of eccentric bicomponent fibers having a PET core and a polyethylene sheath (FIBERVISIONS ETE857G8 PE/PET, 5.7 dtex, 6 mm). The bottom, eucalyptus layer was also sprayed with a 5 gsm polymeric binder in the form of an emulsion (VINNAPAS 192, Wacker+0.8% Aerosol OT75 surfactant). The total weight of the structure was calculated to be 200 gsm.

Sample 6G was a multi-layer unitary structure which was formed on a Danweb Airlaid Pilot Plant. 53 gsm of eucalyptus pulp (Suzann, untreated) was mixed with 7 gsm of bicomponent fibers having a PET core and a polyethylene sheath (TREVIRA Type 255-1663, 2.2 dtex, 3 mm) and deposited on the forming wire. The next layer consisted of 53 gsm of cellulose (Golden Isles® 4723, fully-treated pulp made by GP Cellulose) blended with 22 gsm of high core bicomponent fibers having a PET core a polyethylene sheath with a core to sheath ratio of 7:3 (TREVIRA PE/PET 70% core, 1.7 dtex 6 mm). The top layer was composed of 25 gsm of eccentric bicomponent fibers having a PET core and a polyethylene sheath (FIBERVISIONS ETE857G8 PE/PET, 5.7 dtex, 6 mm). The bottom, eucalyptus layer was also sprayed with a 5 gsm polymeric binder in the form of an emulsion (VINNAPAS 192, Wacker+0.8% Aerosol OT75 surfactant). The total weight of the structure was calculated to be 165 gsm.

Sample 6H was a multi-layer unitary structure which was formed on a Lab Pad Former. 53 gsm of cellulose pulp (Golden Isles® 4723, fully-treated pulp made by GP Cellulose) was mixed with 7 gsm of bicomponent fibers having a PET core and a polyethylene sheath with a core to sheath ratio of 3:7 (TREVIRA PE/PET 30% core, 1.7 dtex 6 mm) and deposited on the wire. The next layer consisted of 80 gsm of cellulose (Golden Isles® 4723, fully-treated pulp made by GP Cellulose) blended with 30 gsm of high core bicomponent fibers having a PET core and a polyethylene sheath with a core to sheath ratio of 7:3 (TREVIRA PE/PET 70% core, 1.7 dtex, 6 mm). The top layer was composed of 25 gsm of eccentric bicomponent fibers have a PET core and a polyethylene sheath (FIBERVISIONS ETE857G8 PE/PET, 5.7 dtex, 6 mm). The bottom, cellulose layer was also sprayed with a 5 gsm polymeric binder in the form of an emulsion (VINNAPAS 192, Wacker+0.8% Aerosol OT75 surfactant). The total weight of the structure was calculated to be 200 gsm.

Table 10, below, provides a pictorial description of the compositions of Samples 6A-6H:

TABLE 10

|  | Layer | Composition |
| --- | --- | --- |
| Sample 6A | Top | 25 gsm eccentric bico (PE/PP, 5.7 dtex, 4 mm) |
|  | Middle | 53 gsm cellulose fluff (GP-4723) |
|  |  | 22 gsm bico (PE/PET, 2.2 dtex, 6 mm) |
|  | SAP | 35 gsm SAP (BASF Favor SXM 7900) |
|  | Bottom | 35 gsm eucalyptus pulp |
|  |  | 7 gsm bico (PE/PET, 2.2 dtex, 3 mm) |
|  |  | 5 gsm Vinnapas 192 with 0.8% surfactant |
| Sample 6B | Top | 25 gsm eccentric bico (PE/PP, 5.7 dtex, 6 mm) |
|  | Middle | 53 gsm cellulose fluff (GP-4723) |
|  |  | 22 gsm concentric bico (PE/PET, 1.7 dtex, 6 mm, 70% core) |
|  | SAP | 35 gsm SAP (BASF Favor SXM 7900) |
|  | Bottom | 53 gsm eucalyptus pulp |
|  |  | 7 gsm bico (PE/PET, 2.2 dtex, 3 mm) |
|  |  | 5 gsm Vinnapas 192 with 0.8% surfactant |
| Sample 6C | Top | 25 gsm eccentric bico (PE/PP, 5.7 dtex, 4 mm) |
|  | Middle | 80 gsm cellulose fluff (GP-4723) |
|  |  | 30 gsm bico (PE/PET, 2.2 dtex, 6 mm) |
|  | Bottom | 53 gsm eucalyptus pulp |
|  |  | 7 gsm bico (PE/PET, 2.2 dtex, 3 mm) |
|  |  | 5 gsm Vinnapas 192 with 0.8% surfactant |
| Sample 6D | Top | 25 gsm eccentric bico (PE/PP, 5.7 dtex, 4 mm) |
|  | Middle | 80 gsm cellulose fluff (GP-4723) |
|  |  | 30 gsm concentric bico (PE/PET, 1.7 dtex, 6 mm, 70% core) |
|  | Bottom | 53 gsm eucalyptus pulp |
|  |  | 7 gsm bico (PE/PET, 2.2 dtex, 3 mm) |
|  |  | 5 gsm Vinnapas 192 with 0.8% surfactant |
| Sample 6E | Top | 25 gsm eccentric bico (PE/PET, 5.7 dtex, 6 mm) |
|  | Middle | 80 gsm cellulose fluff (GP-4723) |
|  |  | 30 gsm concentric bico (PE/PET, 1.7 dtex, 6 mm, 70% core) |
|  | Bottom | 53 gsm eucalyptus pulp |
|  |  | 7 gsm bico (PE/PET, 2.2 dtex, 3 mm) |
|  |  | 5 gsm Vinnapas 192 with 0.8% surfactant |
| Sample 6F | Top | 25 gsm eccentric bico (PE/PET, 5.7 dtex, 6 mm) |
|  | Middle | 80 gsm cellulose fluff (GP-4723) |
|  |  | 30 gsm concentric bico (PE/PET, 1.7 dtex, 6 mm, 70% core) |
|  | Bottom | 53 gsm eucalyptus pulp |
|  |  | 7 gsm bico (PE/PET, 1.7 dtex, 6 mm, 30% core) |
|  |  | 5 gsm Vinnapas 192 with 0.8% surfactant |
| Sample 6G | Top | 25 gsm eccentric bico (PE/PET, 5.7 dtex, 6 mm) |
|  | Middle | 53 gsm cellulose fluff (GP-4723) |
|  |  | 22 gsm concentric bico (PE/PET, 1.7 dtex, 6 mm, 70% core) |
|  | Bottom | 53 gsm eucalyptus pulp |
|  |  | 7 gsm bico (PE/PET, 2.2 dtex, 3 mm) |
|  |  | 5 gsm Vinnapas 192 with 0.8% surfactant |
| Sample 6H | Top | 25 gsm eccentric bico (PE/PET, 5.7 dtex, 6 mm) |
|  | Middle | 80 gsm cellulose fluff (GP-4723) |
|  |  | 30 gsm concentric bico (PE/PET, 1.7 dtex, 6 mm, 70% core) |
|  | Bottom | 53 gsm cellulose fluff (GP-4723) |
|  |  | 7 gsm bico (PE/PET, 1.7 dtex, 6 mm, 30% core) |
|  |  | 5 gsm Vinnapas 192 with 0.8% surfactant |

In addition to Samples 6A-6H, a Control was formed as an absorbent composite composed of two separate layers, stacked one on another. The top layer of the Control served as a liquid acquisition layer whereas the bottom layer was an absorbent core containing superabsorbent powder (SAP). The liquid acquisition layer was a commercially-available 60 gsm latex-bonded airlaid (LBAL) product, Vicell 6609, made by Georgia-Pacific Steinfurt. The absorbent core was a 175 gsm commercially-available multi-bonded airlaid (MBAL), 175 MBS3A, containing SAP, made by Georgia-Pacific Steinfurt.

The liquid acquisition characteristics of the Control and Samples 6A-6H were measured with a synthetic blood solution using the liquid acquisition performance testing procedures described below. Synthetic blood was purchased from Johnson, Moen & Co. Inc. (Rochester, Minn.) (Lot #201141; February 2014). The synthetic blood had a surface tension of 40-44 dynes/cm (ASTM F23.40-F1670) and included various chemicals including ammonium polyacrylate polymer, Azo Red Dye, HPLC distilled water, among other proprietary ingredients. The synthetic blood was diluted with deionized water to a composition of 35% blood and 65% water.

The testing apparatus consists of a 29.2 cm×19.1 cm×0.6 cm hard plastic plate with a 1.9 cm inner diameter hole cut in the center. Attached above the hole was a weighted stainless steel cylinder with a 1.9 cm inner diameter. The cylinder had a height of 5.1 cm, making the complete apparatus a total of 5.7 cm tall and weighing a total of 747.3 g.

Each material (having dimensions 6.5 cm×20.5 cm) was compressed with a 8.190 k plate for 1 minute prior to testing for the liquid acquisition performance using the prepared synthetic blood solution. The material was insulted with 4, 8, or 10 mL of the synthetic blood, depending on the test performed, at a rate of 10 mL/min. The acquisition time was measured from the start of insult until the liquid was no longer visible in the insult cylinder. A total of three insults were performed, yielding acquisition times #1, #2, and #3. The time interval between each of the insults was 10 minutes.

Further, the rewet characteristics of each material were analyzed after measuring the three acquisition times. After the third acquisition time measurement, three pre-weighed square plies (10.1 cm×10.1 cm) of collagen (Colli collagen supplied by Viscofan USA), were placed on top of the tested material. A thin Plexiglas plate and a weight were placed on top of the collagen plies for one minute. The Plexiglas and weight exerted a total pressure of 1.7 kPa. The collagen plies were then weighed to determine the rewet result.

Wicking testing was performed on each sample after Acquisitions #1, 2, and 3 and rewet were completed. The samples were reversed, such that the underside of the core was on top. A standard metric ruler was then used to measure the visible stain lengthwise along the product. This measurement was taken from the outer edge of the stain on one side, to the outer edge of the stain on the other, parallel to the long edge of the product.

For each test, three trials were performed for various insult volumes (4 mL, 8 mL, and 10 mL). All of Samples 6A-6H and the Control were tested with insult volumes of 4 mL. Samples 6A and 6C-6F, as well as the Control, were tested with insult volumes of 8 mL. Samples 6A, 6B, and 6F, as well as the Control, were tested with insult volumes of 10 mL. The average results for each volume, and for each sample are provided in Table 11, below. FIGS. 7A-7C provide the acquisition times, rewet weight, and wicking data for each sample and the Control after testing with 4 mL insults. FIGS. 8A-8C provide the acquisition times, rewet weight, and wicking data for each tested sample and the Control after testing with 8 mL insults. FIGS. 9A-9C provide the acquisition times, rewet weight, and wicking data for each tested sample and the Control after testing with 10 mL insults.

TABLE 11

| Sample | Insult | Acq. Time #1 (s) | Acq. Time #2 (s) | Acq. Time #3 (s) | Rewet Wt. (g) | Thickness (mm) | Sheet wt. (g) | Basis Wt. (gsm) | Wicking (mm) |
|---|---|---|---|---|---|---|---|---|---|
| Control | 4 mL | 25.22 | 29.59 | 49.46 | 0.33 | — | — | — | 84 |
|  | 8 mL | 49.83 | 106.15 | 164.37 | 0.50 | — | — | — | 103.33 |
|  | 10 mL | 62.47 | 158.75 | 232.30 | 0.52 | — | — | — | 148.33 |
| 6A | 4 mL | 25.09 | 27.58 | 34.91 | 0.04 | 3.33 | 2.76 | 216.87 | 107 |
|  | 8 mL | 49.21 | 70.17 | 96.66 | 0.08 | 3.53 | 2.98 | 234.19 | 167 |
|  | 10 mL | 62.92 | 102.28 | 134.45 | 0.12 | — | 2.72 | 214 | 197 |
| 6B | 4 mL | 24.95 | 25.08 | 25.27 | 0.04 | 3.65 | 2.87 | 225.93 | 117 |
|  | 10 mL | 60.90 | 66.20 | 76.64 | 0.12 | — | 2.65 | 209 | 200 |
| 6C | 4 mL | 24.98 | 25.49 | 26.01 | 0.04 | 3.66 | 2.68 | 210.97 | 165 |
|  | 8 mL | 49.38 | 54.67 | 87.40 | 0.21 | 3.65 | 2.64 | 207.82 | 200 |
| 6D | 4 mL | 25.18 | 25.75 | 26.52 | 0.04 | 3.70 | 2.69 | 211.36 | 165 |
|  | 8 mL | 4.22 | 54.66 | 85.76 | 0.19 | 3.61 | 2.52 | 197.98 | 200 |
| 6E | 4 mL | 24.83 | 25.04 | 25.20 | 0.02 | 4.15 | 2.75 | 216.48 | 175 |
|  | 8 mL | 48.83 | 49.04 | 49.29 | 0.08 | 4.00 | 2.65 | 208.61 | 200 |
| 6F | 4 mL | 24.75 | 25.06 | 25.32 | 0.02 | 4.04 | 2.68 | 210.71 | 187 |
|  | 8 mL | 48.77 | 49.12 | 49.26 | 0.08 | 4.17 | 2.72 | 213.86 | 200 |
|  | 10 mL | 60.94 | 61.21 | 63.92 | 0.26 | — | 2.62 | 206 | 200 |
| 6G | 4 mL | 24.88 | 25.11 | 25.37 | 0.02 | 3.47 | 2.22 | 174.37 | 193 |
| 6H | 4 mL | 24.86 | 25.05 | 25.16 | 0.04 | 6.50 | 2.84 | 223.17 | 145 |

As shown in FIGS. 7A, 8A, and 9A, the samples containing high core bicomponent fibers (e.g., Samples 6B and 6D-6H) generally had improved acquisition times as compared to the Control composition material and samples without high core bicomponent fibers (e.g., Samples 6A and 6C), and this effect was more significant at higher insult volumes. Additionally, the samples with high core bicomponent fibers had generally similar or improved rewet and wicking, particularly at lower insult volumes (see, e.g., FIGS. 7B-7C).

To further compare the samples under compression, Samples 6C (without high core bicomponent fibers) and 6D (with high core bicomponent fibers) were placed under a load. The samples were placed between two 35.6 cm×35.6 cm cardboard sheets, and run through a roller press set to a pressure of 4 bar. This compression was done immediately before testing on one set of samples and 1 hour before testing on the second set of samples. The same testing method described earlier in this Example was used to determine the acquisition times, rewet, and wicking. For each test, three trials were performed with insult volumes of 4 mL. The average results for each tested sample prior to compression, immediately after compression, and 1 hour after compression are provided in Table 12, below. Additionally, FIGS. 10A-10C provide the acquisition times, rewet weight, and wicking data for each tested sample.

TABLE 12

| Sample | Timing of Test | Acq. Time #1 (s) | Acq. Time #2 (s) | Acq. Time #3 (s) | Rewet Wt. (g) | Thickness (mm) | Wicking (mm) |
|---|---|---|---|---|---|---|---|
| 6C | prior to compression | 24.98 | 25.49 | 26.01 | 0.04 | 3.66 | 165 |
|  | immediately after compression | 26.83 | 37.59 | 57.01 | 0.08 | 2.22 | 183 |
|  | 1 hour after compression | 25.92 | 33.31 | 47.54 | 0.07 | 2.56 | 177 |
| 6D | prior to compression | 25.18 | 25.75 | 26.52 | 0.04 | 3.70 | 165 |
|  | immediately after compression | 26.27 | 31.17 | 48.05 | 0.06 | 2.17 | 183 |
|  | 1 hour after compression | 25.37 | 30.08 | 42.95 | 0.03 | 2.52 | 182 |

As shown in FIG. 10A, Sample 6D with the high core bicomponent fibers has improved acquisition times after compression as compared to Sample 6C, particularly after repeated insults. Accordingly, these data establish that the high core bicomponent fiber is more resilient than the other bicomponent fibers used in Sample 6C, which allows the internal layer to maintain its structure better than with other fibers. It is surmised that the better acquisition times and lower rewet values (see FIGS. 10A-10B) are the result of the channels within the fibrous network retaining their shape and resisting collapse during compression and/or wetting.

Additionally, the samples of this Example used eucalyptus fiber, which has the benefit of increased wicking. Thus, a greater area of the sample is utilized and liquid is pulled away from the insult area, allowing for better rewet and increased capacity for liquid storage. Because more of the structure is used, it improves the overall functionality as compared to similar basis weight products, particularly composite, non-unitary structures.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various patents and patent applications are cited herein, the contents of which are hereby incorporated by reference herein in their entireties.

What is claimed is:

1. An airlaid nonwoven material, comprising:
   a first layer comprising first high core bicomponent fibers having a polyester core and a polyethylene sheath and a core to sheath ratio of greater than 1:1; and
   a second layer comprising first bicomponent fibers having a core to sheath ratio of less than 1:1 blended with second high core bicomponent fibers having a core to sheath ratio of greater than 1:1.

2. The airlaid nonwoven material of claim 1, where the first high core bicomponent fibers have a core to sheath ratio of about 7:3.

3. The airlaid nonwoven material of claim 1, having a basis weight of from about 50 gsm to about 100 gsm.

4. The airlaid nonwoven material of claim 1, having a caliper of from about 0.1 mm to about 7.5 mm.

5. The airlaid nonwoven material of claim 1, further comprising fine cellulose fibers.

6. The airlaid nonwoven material of claim 1, wherein the first bicomponent fibers of the second layer comprise eccentric bicomponent fibers having a core material selected from the group consisting of polypropylene, poly (ethylene terephthalate), and combinations thereof.

7. The airlaid nonwoven material of claim 1, further comprising:
   a third layer comprising synthetic fibers,
   wherein the first layer further comprises cellulose fibers and is coated on at least a portion of its surface with a binder.

8. An acquisition material, comprising the airlaid nonwoven material of claim 7.

9. An absorbent product, comprising the acquisition material of claim 8 and an absorbent core.

10. The airlaid nonwoven material of claim 1, further comprising:
    a third layer comprising cellulose fibers, wherein the third layer is coated on at least a portion of its surface with a binder.

11. The airlaid nonwoven material of claim 10, wherein the first layer further comprises cellulose fibers.

12. The airlaid nonwoven material of claim 10, further comprising an intermediate SAP layer comprising super absorbent polymer.

13. The airlaid nonwoven material of claim 1, wherein at least one layer comprises a pattern of indentations.

14. An absorbent product, comprising the airlaid nonwoven material of claim 1.

15. An airlaid nonwoven material comprising:
   a first layer comprising a first high core bicomponent fiber having a polyester core and a polyethylene sheath and a core to sheath ratio of greater than 1:1;
   a second layer comprising a first low core bicomponent fiber having a core to sheath ratio of less than 1:1;
   a third layer comprising a bicomponent fiber,
   wherein at least one layer comprises both a bicomponent fiber having a core to sheath ratio of greater than 1:1 and a bicomponent fiber having a core to sheath ratio of less than 1:1.

16. The airlaid nonwoven material of claim 15, wherein at least one layer does not contain a bicomponent fiber having a core to sheath ratio of greater than 1:1.

\* \* \* \* \*